(12) United States Patent
Kwak et al.

(10) Patent No.: US 7,799,054 B2
(45) Date of Patent: Sep. 21, 2010

(54) FACET JOINT REPLACEMENT

(75) Inventors: Seungkyu Daniel Kwak, Grafton, MA (US); John Riley Hawkins, Cumberland, RI (US); Amie Borgstrom, North Attleborough, MA (US); William Dunbar, Norton, MA (US)

(73) Assignee: DePuy Spine, Inc., Raynham, MA (US)

( * ) Notice: Subject to any disclaimer, the term of this patent is extended or adjusted under 35 U.S.C. 154(b) by 308 days.

(21) Appl. No.: 10/908,882

(22) Filed: May 31, 2005

(65) Prior Publication Data

US 2006/0271046 A1      Nov. 30, 2006

Related U.S. Application Data

(63) Continuation-in-part of application No. 10/905,374, filed on Dec. 30, 2004.

(51) Int. Cl.
*A61B 17/70* (2006.01)
(52) U.S. Cl. ...................................................... 606/246
(58) Field of Classification Search ............ 606/60–61, 606/72–73, 246, 247, 250, 251, 252, 257, 606/258, 259; 623/17.11–17.16
See application file for complete search history.

(56) References Cited

U.S. PATENT DOCUMENTS

| | | | |
|---|---|---|---|
| 3,648,691 A | 3/1972 | Lumb et al. |
| 3,693,616 A | 9/1972 | Roaf et al. |
| 4,448,191 A | 5/1984 | Rodnyansky et al. |
| 4,743,260 A | 5/1988 | Burton |
| 5,084,049 A | 1/1992 | Asher et al. |
| 5,092,866 A | 3/1992 | Beard |
| 5,152,303 A | 10/1992 | Allen |
| 5,176,680 A | 1/1993 | Vignaud et al. |
| 5,190,543 A | 3/1993 | Schlapfer |
| 5,261,911 A | 11/1993 | Carl |
| 5,282,863 A | 2/1994 | Burton |
| 5,306,275 A | 4/1994 | Bryan |
| 5,360,429 A | 11/1994 | Jeanson et al. |
| 5,375,823 A | 12/1994 | Navas et al. |
| 5,387,213 A | 2/1995 | Breard et al. |
| 5,403,316 A | 4/1995 | Ashman |
| 5,415,661 A | 5/1995 | Holmes |

(Continued)

FOREIGN PATENT DOCUMENTS

EP      0576379 A1      12/1993

(Continued)

OTHER PUBLICATIONS

EP Search Report, Application No. 05849737.1, Aug. 6, 2009.

*Primary Examiner*—Eduardo C Robert
*Assistant Examiner*—Elana B Fisher
(74) *Attorney, Agent, or Firm*—Nutter McClennen & Fish LLP

(57) ABSTRACT

Various methods and devices for replacing damaged, injured, diseased, or otherwise unhealthy posterior elements, such as the facet joints, the lamina, the posterior ligaments, and/or other features of a patient's spinal column, are provided. In one exemplary embodiment, the methods and devices are effective to mimic the natural function of the spine by allowing flexion, extension, and lateral bending of the spine, while substantially restricting posterior-anterior shear and rotation of the spine.

18 Claims, 18 Drawing Sheets

U.S. PATENT DOCUMENTS

| | | | |
|---|---|---|---|
| 5,425,732 A | 6/1995 | Ulrich et al. |
| 5,437,669 A | 8/1995 | Yuan et al. |
| 5,437,671 A | 8/1995 | Lozier et al. |
| 5,474,086 A | 12/1995 | McCormick et al. |
| 5,486,174 A | 1/1996 | Fournet-Fayard et al. |
| 5,496,318 A | 3/1996 | Howland et al. |
| 5,540,688 A | 7/1996 | Navas |
| 5,556,431 A | 9/1996 | Buttner-Janz |
| 5,562,737 A | 10/1996 | Graf |
| 5,571,191 A | 11/1996 | Fitz |
| 5,591,165 A | 1/1997 | Jackson |
| 5,601,554 A | 2/1997 | Howland et al. |
| 5,672,175 A | 9/1997 | Martin |
| 5,681,312 A | 10/1997 | Yuan et al. |
| 5,716,355 A | 2/1998 | Jackson |
| 5,725,582 A | 3/1998 | Bevan et al. |
| 5,733,284 A | 3/1998 | Martin et al. |
| 5,755,796 A | 5/1998 | Ibo et al. |
| 5,766,254 A | 6/1998 | Gelbard |
| 5,810,815 A * | 9/1998 | Morales ...................... 606/250 |
| RE36,221 E | 6/1999 | Breard et al. |
| 5,928,233 A | 7/1999 | Apfelbaum et al. |
| 5,938,663 A | 8/1999 | Petreto |
| 5,961,516 A | 10/1999 | Graf |
| 6,019,760 A | 2/2000 | Metz-Stavenhagen et al. |
| RE36,758 E | 6/2000 | Fitz |
| 6,132,464 A | 10/2000 | Martin |
| 6,241,730 B1 | 6/2001 | Alby |
| 6,248,106 B1 | 6/2001 | Ferree |
| 6,267,764 B1 | 7/2001 | Elberg |
| 6,273,888 B1 | 8/2001 | Justis |
| 6,355,038 B1* | 3/2002 | Pisharodi ...................... 606/300 |
| 6,364,883 B1 | 4/2002 | Santilli |
| 6,419,703 B1 | 7/2002 | Fallin |
| 6,440,169 B1 | 8/2002 | Elberg et al. |
| 6,468,276 B1 | 10/2002 | McKay |
| 6,547,790 B2 | 4/2003 | Harkey et al. |
| 6,551,322 B1 | 4/2003 | Lieberman |
| 6,551,332 B1 | 4/2003 | Nguyen et al. |
| 6,554,831 B1 | 4/2003 | Rivard et al. |
| 6,554,832 B2 | 4/2003 | Shluzas |
| 6,565,605 B2 | 5/2003 | Goble |
| 6,579,319 B2 | 6/2003 | Goble |
| 6,610,091 B1 | 8/2003 | Reiley |
| 6,626,904 B1 | 9/2003 | Jammet et al. |
| 6,626,909 B2 | 9/2003 | Chin |
| 6,626,944 B1 | 9/2003 | Taylor |
| 6,645,207 B2 | 11/2003 | Dixon et al. |
| 6,669,729 B2 | 12/2003 | Chin |
| 6,811,567 B2 | 11/2004 | Reiley |
| 7,011,685 B2* | 3/2006 | Arnin et al. .............. 623/17.16 |
| 7,074,237 B2 | 7/2006 | Goble et al. |
| 7,104,992 B2 | 9/2006 | Bailey |
| 7,189,236 B2 | 3/2007 | Taylor et al. |
| 7,270,665 B2 | 9/2007 | Morrison et al. |
| 2002/0029039 A1 | 3/2002 | Zucherman et al. |
| 2002/0055740 A1 | 5/2002 | Lieberman |
| 2002/0065557 A1 | 5/2002 | Goble et al. |
| 2002/0072800 A1 | 6/2002 | Goble et al. |
| 2002/0123806 A1 | 9/2002 | Reiley |
| 2002/0133155 A1 | 9/2002 | Ferree |
| 2002/0151978 A1 | 10/2002 | Zacouto et al. |
| 2003/0004572 A1 | 1/2003 | Goble et al. |
| 2003/0028250 A1 | 2/2003 | Reiley et al. |
| 2003/0055427 A1 | 3/2003 | Graf |
| 2003/0083657 A1 | 5/2003 | Drewry |
| 2003/0093078 A1* | 5/2003 | Ritland ...................... 606/73 |
| 2003/0109880 A1 | 6/2003 | Shirado et al. |
| 2003/0135277 A1 | 7/2003 | Bryan et al. |
| 2003/0153912 A1 | 8/2003 | Graf |
| 2003/0171749 A1 | 9/2003 | Le Couedic et al. |
| 2003/0171750 A1 | 9/2003 | Chin |
| 2003/0176926 A1 | 9/2003 | Boehm et al. |
| 2003/0187438 A1 | 10/2003 | Assaker et al. |
| 2003/0187454 A1 | 10/2003 | Gill et al. |
| 2003/0191470 A1 | 10/2003 | Ritland |
| 2003/0191532 A1 | 10/2003 | Goble et al. |
| 2003/0220642 A1 | 11/2003 | Freudiger |
| 2003/0220643 A1 | 11/2003 | Ferree |
| 2004/0002708 A1 | 1/2004 | Ritland |
| 2004/0006391 A1 | 1/2004 | Reiley |
| 2004/0015174 A1 | 1/2004 | Null et al. |
| 2004/0049189 A1 | 3/2004 | Le Couedic et al. |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0073215 A1 | 4/2004 | Carli |
| 2004/0097950 A1 | 5/2004 | Foley et al. |
| 2004/0111154 A1 | 6/2004 | Reiley |
| 2004/0116927 A1 | 6/2004 | Graf |
| 2004/0127989 A1 | 7/2004 | Dooris et al. |
| 2004/0133203 A1 | 7/2004 | Young et al. |
| 2004/0138660 A1 | 7/2004 | Serhan |
| 2004/0143264 A1 | 7/2004 | McAfee |
| 2004/0147928 A1 | 7/2004 | Landry et al. |
| 2004/0186475 A1 | 9/2004 | Falahee |
| 2004/0186575 A1 | 9/2004 | Varga et al. |
| 2004/0236329 A1 | 11/2004 | Panjabi |
| 2004/0249379 A1 | 12/2004 | Winslow et al. |
| 2004/0267259 A1 | 12/2004 | Mazda et al. |
| 2005/0033431 A1 | 2/2005 | Gordon et al. |
| 2005/0033432 A1 | 2/2005 | Gordon et al. |
| 2005/0033434 A1 | 2/2005 | Berry |
| 2005/0033439 A1 | 2/2005 | Gordon et al. |
| 2005/0049708 A1 | 3/2005 | Atkinson et al. |
| 2005/0055096 A1 | 3/2005 | Serhan et al. |
| 2005/0101954 A1 | 5/2005 | Simonson |
| 2005/0101956 A1 | 5/2005 | Simonson |
| 2005/0113927 A1 | 5/2005 | Malek |
| 2005/0119748 A1* | 6/2005 | Reiley et al. ............. 623/17.11 |
| 2005/0131409 A1 | 6/2005 | Chervitz et al. |
| 2005/0171610 A1 | 8/2005 | Humphreys et al. |
| 2005/0203518 A1 | 9/2005 | Biedermann et al. |
| 2005/0228381 A1 | 10/2005 | Kirschman |
| 2005/0228501 A1 | 10/2005 | Miller et al. |
| 2005/0240265 A1 | 10/2005 | Kuiper et al. |
| 2005/0245929 A1 | 11/2005 | Winslow et al. |
| 2005/0256578 A1 | 11/2005 | Blatt et al. |
| 2005/0277922 A1 | 12/2005 | Trieu et al. |
| 2005/0277930 A1 | 12/2005 | Parsons |
| 2006/0036240 A1 | 2/2006 | Colleran et al. |
| 2006/0052785 A1 | 3/2006 | Augostino et al. |
| 2006/0079896 A1 | 4/2006 | Kwak et al. |
| 2006/0084976 A1 | 4/2006 | Borgstrom et al. |
| 2006/0084984 A1 | 4/2006 | Kim |
| 2006/0084991 A1 | 4/2006 | Borgstrom et al. |
| 2006/0129239 A1 | 6/2006 | Kwak |
| 2006/0149229 A1 | 7/2006 | Kwak et al. |
| 2006/0149230 A1 | 7/2006 | Kwak et al. |
| 2006/0189983 A1* | 8/2006 | Fallin et al. .................. 606/61 |
| 2006/0200130 A1* | 9/2006 | Hawkins et al. ............... 606/61 |
| 2006/0241771 A1 | 10/2006 | Gordon et al. |
| 2006/0265074 A1 | 11/2006 | Krishna et al. |
| 2006/0271046 A1 | 11/2006 | Kwak et al. |

FOREIGN PATENT DOCUMENTS

| | | |
|---|---|---|
| EP | 0669109 | 2/1994 |

| | | | | | | |
|---|---|---|---|---|---|---|
| EP | 0612507 | A1 | 8/1994 | WO | 02102259 | 12/2002 |
| EP | 0669109 | A1 | 8/1995 | WO | WO-02/102259 | 12/2002 |
| EP | 1153577 | | 11/2001 | WO | 03007828 A1 | 1/2003 |
| FR | 2694182 | A | 2/1994 | WO | WO-03/007828 | 1/2003 |
| FR | 2694182 | A1 | 2/1994 | WO | 03009737 A1 | 2/2003 |
| FR | 2697428 | A1 | 5/1994 | WO | WO-03/009737 | 2/2003 |
| FR | 2701833 | A1 | 9/1994 | WO | 2004024011 A1 | 3/2004 |
| WO | WO-01/45576 | | 6/2001 | WO | WO-2004/024011 | 3/2004 |
| WO | 0217803 | A2 | 3/2002 | WO | 2004034916 A1 | 4/2004 |
| WO | WO-02/17803 | | 3/2002 | WO | WO-2004/034916 | 4/2004 |
| WO | 0243603 | A1 | 6/2002 | | | |
| WO | WO-02/43603 | | 6/2002 | | | |

* cited by examiner

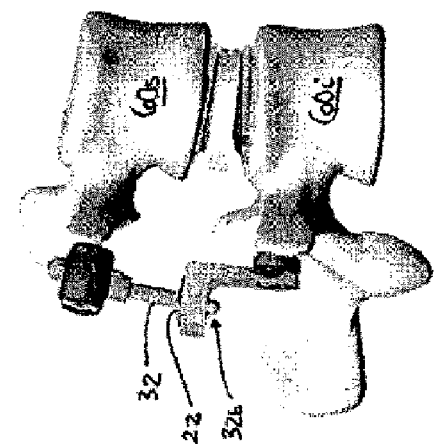
FIG. 4C  Flexion
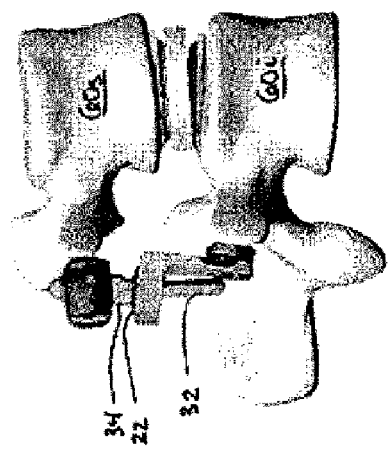
FIG. 4B  Extension
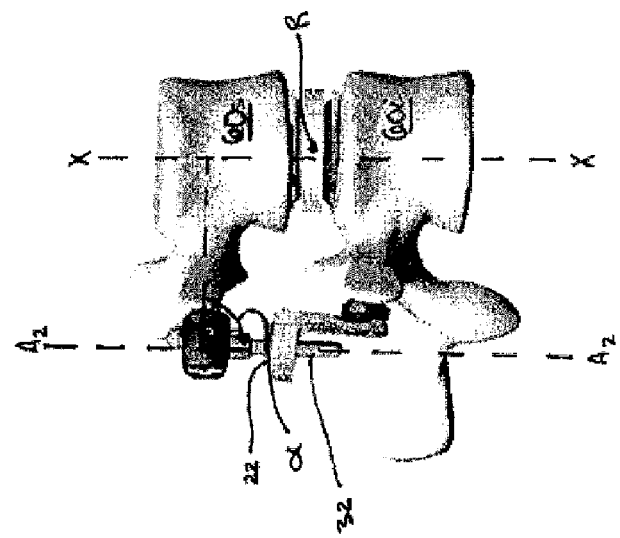
FIG. 4A  Neutral

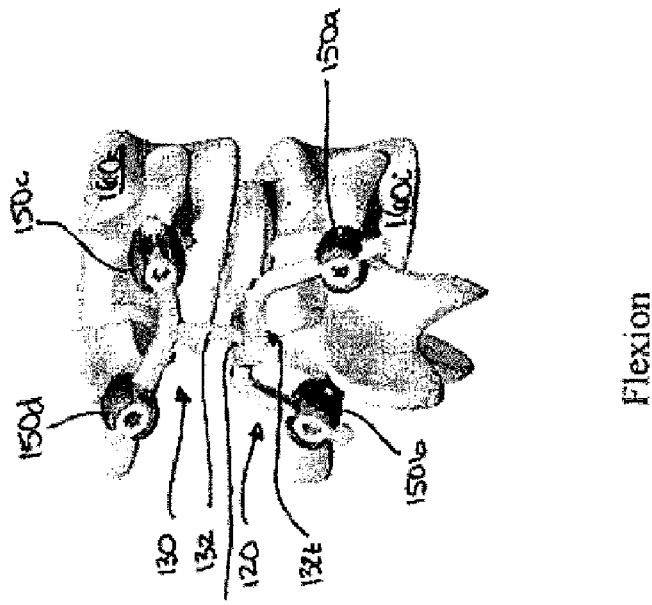
FIG. 8C — Flexion
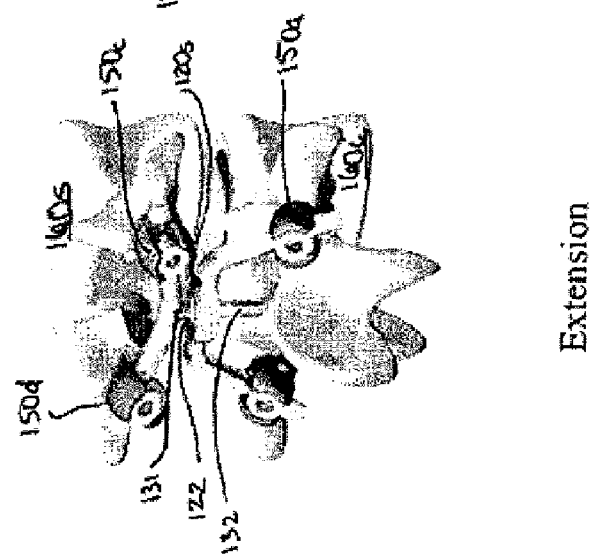
FIG. 8B — Extension
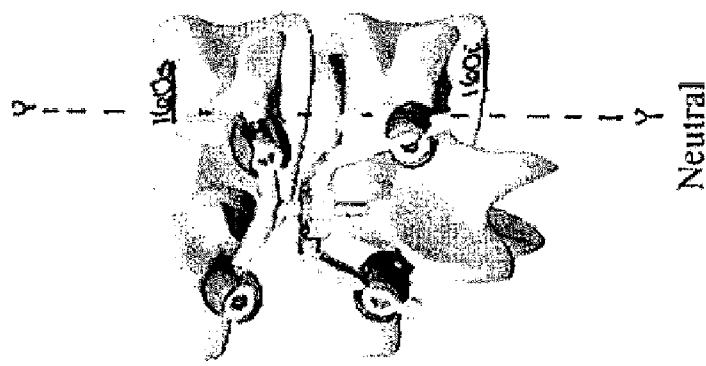
FIG. 8A — Neutral

FACET JOINT REPLACEMENT

CROSS REFERENCE TO RELATED APPLICATIONS

This application is a continuation-in-part of U.S. patent application Ser. No. 10/905,374 filed on Dec. 30, 2004 and entitled "Artificial Facet Joint," which is hereby incorporated herein in its entirety.

FIELD OF THE INVENTION

The present invention relates to spinal instrumentation, and in particular to various devices that are adapted to mimic the natural function of the structural posterior elements.

BACKGROUND OF THE INVENTION

The vertebrae in a patient's spinal column are linked to one another by the disc and the facet joints, which control movement of the vertebrae relative to one another. Each vertebra has a pair of articulating surfaces located on the left side, and a pair of articulating surfaces located on the right side, and each pair includes a superior articular surface, which faces upward, and an inferior articular surface, which faces downward. Together the superior and inferior articular surfaces of adjacent vertebra form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Diseased, degenerated, impaired, or otherwise painful facet joints and/or discs can require surgery to restore function to the three joint complex. Subsequent surgery may also be required after a laminectomy, as a laminectomy predisposes the patient to instability and may lead to post-laminectomy kyphosis (abnormal forward curvature of the spine), pain, and neurological dysfunction. Damaged, diseased levels in the spine were traditionally fused to one another. While such a technique may relieve pain, it effectively prevents motion between at least two vertebrae. As a result, additional stress may be applied to the adjoining levels, thereby potentially leading to further damage.

More recently, techniques have been developed to restore normal function to the facet joints. One such technique involves covering the facet joint with a cap to preserve the bony and articular structure. Capping techniques, however, are limited in use as they will not remove the source of the pain in osteoarthritic joints. Caps are also disadvantageous as they must be available in a variety of sizes and shapes to accommodate the wide variability in the anatomical morphology of the facets. Caps also have a tendency to loosen over time, potentially resulting in additional damage to the joint and/or the bone support structure containing the cap.

Other techniques for restoring the normal function to the posterior element involve arch replacement, in which superior and inferior prosthetic arches are implanted to extend across the vertebra. The arches may have rigid surfaces that can articulate relative to one another to replace the articulating function of the facet joints. However, aligning two articulating rigid surfaces for facet replacements can be very difficult given the variations in patient anatomy and various motion required (i.e., flexion, extension, lateral bending, and translations).

Accordingly, there remains a need for improved systems and methods that are adapted to mimic the natural function of the facet joints.

BRIEF SUMMARY OF THE INVENTION

The present invention provides various methods and devices for repairing and/or replacing a damaged facet joint, and optionally for replacing other posterior elements, including, for example, the lamina, the posterior ligaments, and/or other features of a patient's spinal column. In one exemplary embodiment, an implant for replacing and/or stabilizing one or more facet joints in a patient's spinal column is provided and it generally includes a first member that is adapted to couple to a first vertebra, and a second member that is adapted to couple to a second vertebra and that is configured to move relative to the first member to control movement of the adjacent vertebrae. In certain exemplary embodiments, the implant can be configured to limit axial rotation and shearing, while allowing or controlling flexion, extension, and lateral bending.

While the implant can have a variety of configurations, in one exemplary embodiment the implant can include a first member that is adapted to couple to a first vertebra and that has a bearing element rotatably disposed therein with an opening formed therethrough, and a second member that is adapted to couple to a second vertebra adjacent to the first vertebra. The second member can include an extension rod that is adapted to extend through the opening formed in the bearing element to control movement between the first and second vertebrae.

While the first and second members can have a variety of configurations, in one exemplary embodiment the first member can be substantially U-shaped with opposed arms extending from a central portion, and the second member can be substantially Y-shaped with opposed arms extending from a terminal end of the extension rod. In use, each arm on the first and second members can be adapted to be received within a receiving head of a bone engaging element, such as a bone screw, to attach each arm to a vertebra. The implant can also include at least one compressive element positioned between the central portion of the first member and the central portion of the second member, and at least one compressive element positioned between the central portion of the second member and a terminal end of the extension rod. The compressive element(s) can be adapted to facilitate controlled movement of the adjacent vertebrae.

The bearing element can also have a variety of configurations, but in one exemplary embodiment the bearing element can be a ball bearing having an opening formed therethrough. The opening formed through the bearing element can include a coating formed thereon that is adapted to reduce friction between the bearing element and the extension rod. The bearing element can also be disposed at various locations on the first member, but in one exemplary embodiment the bearing element can be freely rotatably disposed within the central portion of the first member. In particular, the central portion can include a substantially spherical opening formed therein for rotatably seating the bearing element.

In another embodiment of the invention, the extension rod can include at least one stop member formed thereon and adapted to limit slidable movement of the extension rod relative to the bearing element. For example, the extension rod can include first and second stop members formed on first and second terminal ends thereof. The stop member(s) can have a variety of configurations, and it can be formed from a variety of materials including, for example, a compressive material. In one embodiment, the stop member(s) can be in the form of a ring-shaped member that is disposed around the extension rod. An exemplary ring-shaped member has a diameter that is greater than a diameter of the opening in the bearing element.

In yet another embodiment, the first member can be substantially L-shaped with a first portion that is adapted to mate to a bone engaging element, and a second portion having the bearing element rotatably disposed therein. The first portion of the first member can include an opening formed therein for receiving a portion of a locking mechanism adapted to couple the first portion of the first member to a bone engaging element. The first portion of the first member can also include an articulating surface formed thereon and that is adapted to be received within a complementary surface formed on a bone engaging element. In one exemplary embodiment, the articulating surface can be substantially spherical.

In another exemplary embodiment, the second member can be a substantially elongate member having a first portion that is adapted to mate to a bone engaging element and a second portion that is adapted to be disposed through the bearing element. The first and second portions of the second member can be axially offset from one another. The second member can also include a stop formed thereon between the first and second portions. The stop can be adapted to limit movement of the second portion relative to the bearing.

One exemplary method for stabilizing the posterior element in adjacent vertebrae is also provided. The method can include coupling a first member to a first vertebra and a second member to a second vertebra such that an extension rod on the first member extends through a bearing element rotatably disposed within the second member to control movement of the first and second vertebrae relative to one another. The method can also include positioning the extension rod at a predetermined angle relative to a central axis of the first and second vertebrae.

In one exemplary embodiment, the first member can be coupled to the first vertebra by implanting first and second bone engaging members in the first vertebra and mating a portion of the first member to the first and second bone engaging members, and the second member can be coupled to the second vertebra by implanting first and second bone engaging members in the second vertebra and mating a portion of the second member to the first and second bone engaging members. The first and second bone engaging members can be implanted an opposed lateral sides of each vertebra.

In another exemplary embodiment, the first member can be coupled to the first vertebra by implanting a bone engaging member in the first vertebra and mating a portion of the first member to the bone engaging member, and the second member can be coupled to the second vertebra by implanting a bone engaging member in the second vertebra and mating a portion of the second member to the bone engaging member.

In other aspects, an implant for stabilizing the spine is provided and it can include a first member that is adapted to rigidly couple to a first vertebra, and a second member that is adapted to movably couple to a second vertebra. The second member can be slidably coupled to and movable relative to the first member to control movement of first and second vertebrae coupled thereto.

While the first and second members can have a variety of configurations, in one exemplary embodiment the first member can include a first lateral portion having a lumen extending therethrough, a second lateral portion having a lumen extending therethrough, and a connecting member extending between and coupled to the first and second lateral portions. The second member can include a first pin member slidably disposed through the first lateral portion, and a second pin member slidably disposed through the second lateral portion. In one exemplary embodiment, the first and second pin members each include a head formed on a terminal end thereof and adapted to be received within a portion of the lumen in the first and second lateral portions. In certain exemplary embodiments, the lumens in the first and second lateral portions can each include a stop formed therein and adapted to limit slidably movement of the head of the pin member.

In other embodiments, the implant can include at least one compressive member disposed between the first and second members and adapted to compress to limit extension of first and second vertebrae coupled to the first and second members. In one exemplary embodiment, the implant can include a compressive member disposed on each pin member and adapted to compress as the pin member slidably moves relative to the first and second lateral portions of the first member.

A variety of techniques are also provided for movably coupled the second member to a vertebra. In one embodiment, the pin members can couple to a polyaxial bone screw that allows movement of the second member relative to the vertebra. In another embodiment, a terminal end of each of the first and second pin members can include a spherical member formed thereon and adapted to be rotatably received within a fastening element, such as a monoaxial bone screw, for movably coupling the pin members to a second vertebra.

The connecting member that couples the first and second members can also have a variety of configurations, but in one exemplary embodiment the connecting member can be in the form of an elongate bar having opposed terminal ends that are adapted to mate to the first and second lateral portions. The first and second lateral portions can include offset connectors formed thereon, and the offset connectors and the opposed terminal ends of the connecting member can include bores formed therein for receiving a bone screw to mate the first member to a first vertebra. In certain exemplary embodiments, one or more washers can be provided to allow a bone screw inserted therethrough and through the offset connector and connecting member to be positioned at an angle relative to an axis of the bore formed in at least one of the terminal ends of the connecting member. The washer can have a variety of configurations including, for example, an angled configuration or a polyaxial configuration.

In another exemplary embodiment, an implant for stabilizing the spine is provided and it includes a first member having a first portion adapted to rigidly couple to a first vertebra, and a second portion slidably movable with respect to the first portion and adapted to couple to a second vertebra, and a second member having a first portion adapted to rigidly couple to a first vertebra, and a second portion slidably movable with respect to the first portion and adapted to couple to a second vertebra. A connecting member can extend between and couple to the first and second members. The first and second members can also each include a compressible member disposed around a portion of the second portion and adapted to compress upon slidable movement of the second portion relative to the first portion.

The second portion of each of the first and second members can have a variety of configurations, but in one exemplary embodiment the second portions can be in the form of pin members that are slidably disposed through the first portions. The pin members can mate to a second vertebra using a variety of techniques, but in one exemplary embodiment each pin member can be received within the head of a bone screw. The head of the bone screw can be polyaxial, or it can be rigid and the pin member can include a spherical member formed on the head thereof for providing a polyaxial connection.

In another aspect, a method for stabilizing the posterior element in adjacent vertebrae is provided. The method can include rigidly coupling a first member to a first vertebra, and movably coupling a second member to a second vertebra. The second member can be slidably movable relative to the first member to control movement of the first and second vertebrae relative to one another. In one embodiment, the first and second members can substantially prevent axial rotation of the first and second vertebrae relative to one another. In another embodiment, the first and second members can limit extension of the first and second vertebrae relative to one another. In yet another embodiment, the first and second members can control lateral bending and flexion of the first and second vertebrae relative to one another.

In yet another exemplary embodiment, a method for stabilizing adjacent vertebrae is provided and includes accessing a spinal column having a dynamic implant with first and second members coupled to first and second adjacent vertebrae, the first and second members being movable relative to one another to control movement of the adjacent vertebrae coupled thereto, and coupling a locking mechanism to the first and second members to substantially prevent movement of the first and second members relative to one another, thereby converting the dynamic implant into a rigid implant.

BRIEF DESCRIPTION OF THE DRAWINGS

The invention will be more fully understood from the following detailed description taken in conjunction with the accompanying drawings, in which:

FIG. 4A is a side view of one of the posterior stabilizing implants shown in FIG. 1A showing the adjacent vertebrae in a neutral position;

FIG. 4B is a side view of one of the posterior stabilizing implants shown in FIG. 1A showing extension of the adjacent vertebrae;

FIG. 4C is a side view of one of the posterior stabilizing implants shown in FIG. 1A showing flexion of the adjacent vertebrae

FIG. 8A is a side view of the posterior stabilizing implant shown in FIG. 5A showing the adjacent vertebrae in a neutral position;

FIG. 8B is a side view of the posterior stabilizing implant shown in FIG. 5A showing extension of the adjacent vertebrae;

FIG. 8C is a side view of the posterior stabilizing implant shown in FIG. 5A showing flexion of the adjacent vertebrae;

DETAILED DESCRIPTION OF THE INVENTION

The present invention provides various methods and devices for replacing damaged, injured, diseased, or otherwise unhealthy posterior elements, such as the facet joints, the lamina, the posterior ligaments, and/or other features of a patient's spinal column. In one exemplary embodiment, a posterior stabilizing implant is provided and it includes at least two members that are adapted to move relative to one another to mimic the natural function of the spine by allowing or controlling flexion, extension, and lateral bending of the spine, preferably while substantially restricting posterior-anterior shear and rotation of the spine. A person skilled in the art will appreciate that, while the methods and devices are especially configured for use in restoring and/or replacing the facet joints and optionally other posterior elements of a patient's spine, the methods and devices can be used for a variety of other purposes in a variety of other surgical procedures.

Figure 1A:
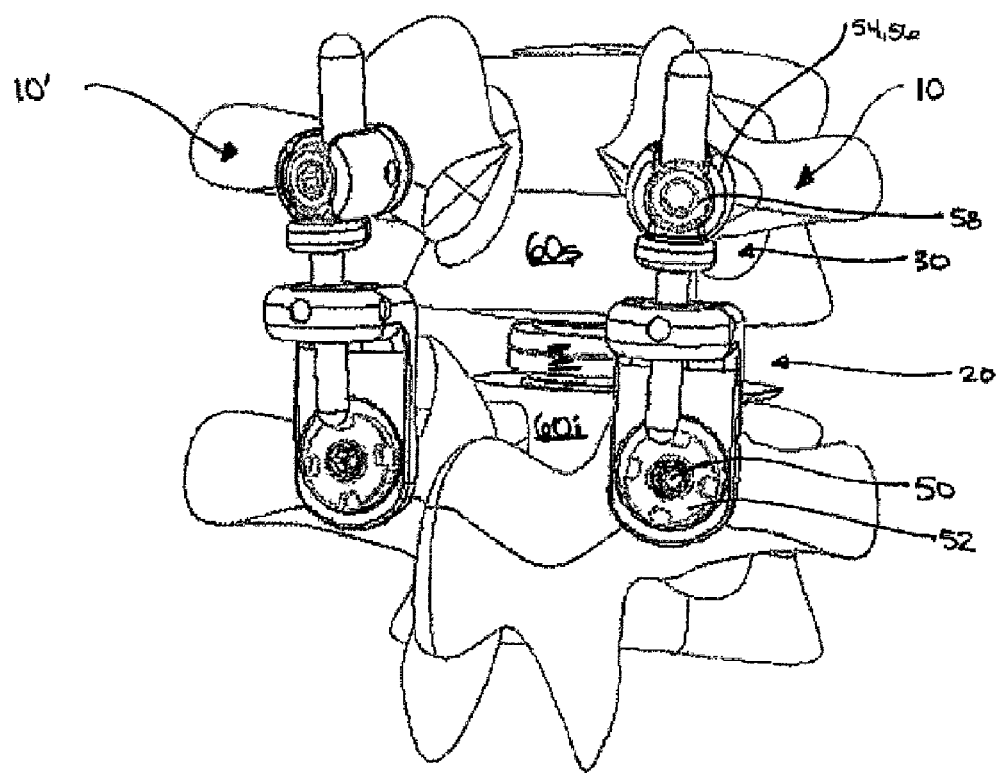
FIG. 1A is perspective view of two exemplary posterior stabilizing implants coupled to adjacent vertebrae.

FIGS. 1A-4C illustrate one exemplary embodiment of a posterior stabilizing implant. While two implants 10, 10' are shown coupled to opposed lateral sides of two adjacent vertebrae 60s, 60i, only one implant 10 will be discussed herein. A person skilled in the art will understand that the implants 10, 10' can have substantially the same configuration. Moreover, while only two implants 10, 10' are shown, additional implants can be coupled to additional vertebrae located along the patient's spinal column. FIGS. 1A-1B also illustrate an artificial disc/implanted between the adjacent vertebrae 60s, 60i. A person skilled in the art will appreciate that the posterior stabilizing implants disclosed herein can be used with a natural disc or with an artificial disc. In an exemplary embodiment, where an artificial disc is used, the disc is preferably one which allows movement of the adjacent vertebrae 60s, 60i relative to one another. By way of non-limiting example, one exemplary artificial disc for use with the present invention is the Charité™ Artificial Disc available from DePuy Spine, Inc.

Figure 1B:
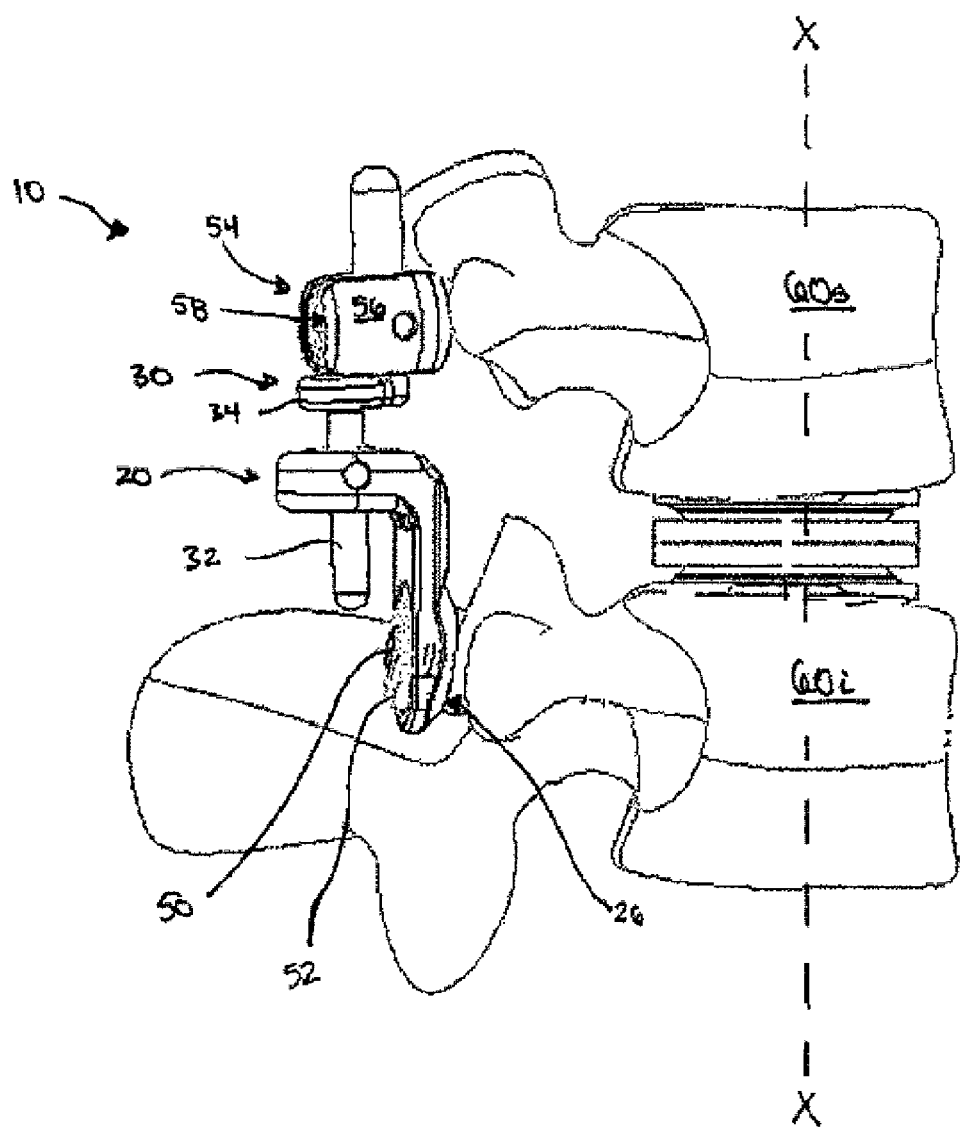
FIG. 1B is a side view of one of the posterior stabilizing implants shown in FIG. 1A coupled to adjacent vertebrae.

As shown in FIGS. 1A-1B, the implant 10 can include a first member 20 that is coupled to a first vertebra, e.g., the inferior vertebra 60i, and a second member 30 that is coupled to a second vertebra, e.g., the superior vertebra 60s. While not shown, the first and second members 20, 30 can be reversed such that the first member 20 is coupled to the superior vertebra 60s and the second member 30 is coupled to the inferior vertebra 60i. The first and second members 20, 30 can also be movably coupled to one another. In particular, the first member 20 can include a bearing element 22 movably disposed therein, and the second member 30 can include an extension rod 32 that is adapted to slidably extend through the bearing element 22. In use, the bearing element 22 and the extension rod 32 cooperate to control movement of the superior and inferior vertebrae 60s, 60i relative to one another, and in particular they allow flexion, extension, and lateral bending of the vertebrae 60s, 60i, while substantially restricting posterior-anterior shear and rotation of the vertebrae 60s, 60i.

Figure 2B:
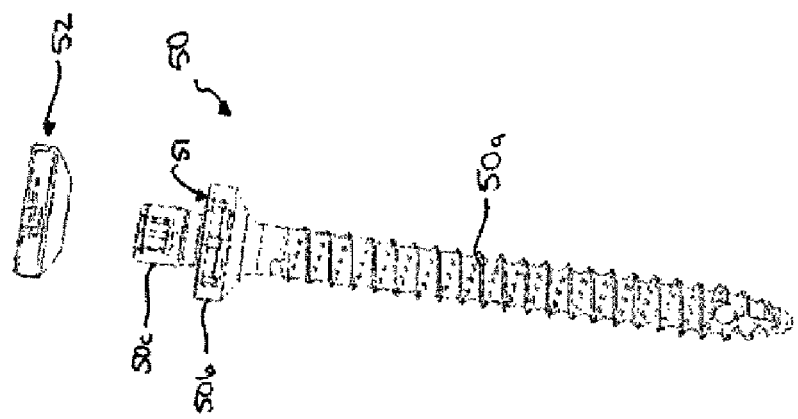
FIG. 2B is a perspective view of one exemplary embodiment of a bone screw and a locking mechanism for use with the first member shown in FIG. 2A.
Figure 2A:
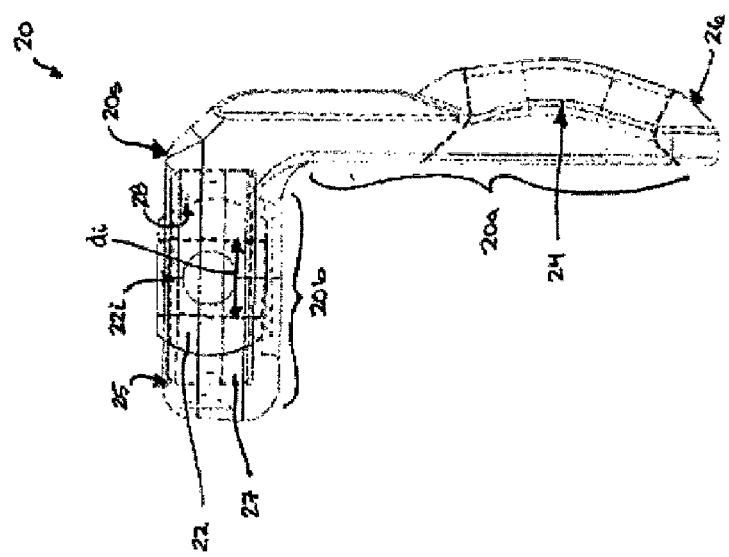
FIG. 2A is a side view of a first member of one of the exemplary implants shown in FIG. 1A.

The first member 20 of the implant 10, which is shown in more detail in FIG. 2A, can have a variety of configurations. In the illustrated exemplary embodiment, however, the first member 20 is substantially L-shaped and it includes a first portion 20a that is adapted to mate to a vertebra, e.g., the inferior vertebra 60i, and a second portion 20b having the bearing element 22 disposed therein. The exemplary first and second portions 20a, 20b each have a substantially planar configuration, and each portion 20a, 20b can be positioned at an angle relative to one another. For example, the first and second portions 20a, 20b can be substantially perpendicular to one another. The configuration of each portion 20a, 20b relative to one another can, however, vary depending on the intended use.

As noted above, the first portion 20a is adapted to mate to a vertebra. While various techniques can be used to allow the first portion 20a to mate to a vertebra, in the illustrated exemplary embodiment the first portion 20a includes an opening 24 extending therethrough for receiving a portion of a fastening element and/or a bone engaging element. The opening 24 can vary in shape and size depending on the type of bone engaging element and fastening element being used. In an exemplary embodiment, as shown in FIG. 2B, the bone engaging element is a bone screw 50 and the fastening element is a locking nut 52 that is adapted to engage the bone screw 50 to lock the first portion 20a of the first element 20 relative to the vertebra 60i. In particular, the bone screw 50 has a threaded shank 50a that is adapted to extend into the vertebra 60i, a receiving head 50b formed on the threaded shank 50a, and a threaded central shaft 50c that extends from the receiving head 50b through the opening 24 in the first portion 20a and that mates to the locking nut 52. In one exemplary embodiment the receiving head 50b can have a shape that is configured to seat a posterior surface or articulating surface 26 of the first portion 20a of the first member 20 such that a position of the first member 20 relative to the bone screw 50 can be adjusted. For example, the receiving head 50b can include a substantially spherical recess 51 formed therein, and the articulating surface 26 of the first portion 20a of the first member 20 can be substantially spherical, as shown in FIG. 2A. As a result, the first member 20 can be angularly adjustable relative to the bone screw 50, and in particular relative to the vertebra 60i. Such a configuration allows the bearing element 22 of the second portion 20b of the first member 20 to be positioned as desired, as will be discussed in more detail below.

The second portion 20b of the first member 20 can also have a variety of configurations, but as noted above the exemplary second portion 20b includes a bearing element 22 disposed therein for receiving the extension rod 32 on the second member 30. Various bearing elements 22 known in the art can be used, but in the illustrated embodiment the bearing element 22 is a standard ball bearing that includes an opening 22i formed therethrough. The bearing element 22 can be disposed within the second portion 20b of the first member 20 using a variety of techniques, but in an exemplary embodiment the bearing element 22 is preferably freely rotatable relative to the second portion 20b of the first member 20. This will allow the bearing element 22 to pivot/rotate as the first and second members 20, 22 move relative to one another as a result of movement of the vertebrae 60s, 60i relative to one another. As shown in FIG. 2A, the bearing element 22 is disposed within a spherical recess 28 that is formed within and extends through an insert 27, and the insert 27 in turn is disposed within an opening 25 formed in the second portion 20b. A person skilled in the art will understand that the bearing element 22 can be directly disposed within a recess formed within the second portion 20b, and the use of an insert 27 is not necessary.

In order to facilitate free rotation/movement of the bearing element 22 within the recess 28, the bearing element 22 and/or the recess 28 can include a coating to reduce friction and reduce wear. The opening 22i in the bearing element 22 can also include a coating formed therein to reduce friction and wear on the bearing element 22 caused by movement of the extension rod 32 therethrough. Suitable exemplary materials for coating the bearing element 22, the recess 28, and/or the extension rod 32 include, by way of non-limiting example, titanium nitrite coating, titanium carbon-nitrite coating, diamond-like carbon coating, and other similar materials. The bearing element 22, the recess 28, and/or the extension rod 32, which will be discussed in more detail below, can also be formed from certain materials that are adapted to withstand wear, such as, for example, stainless steel, titanium, cobalt chrome, plastics such as polyethylene and polyurethane, and various ceramics.

Figure 3:
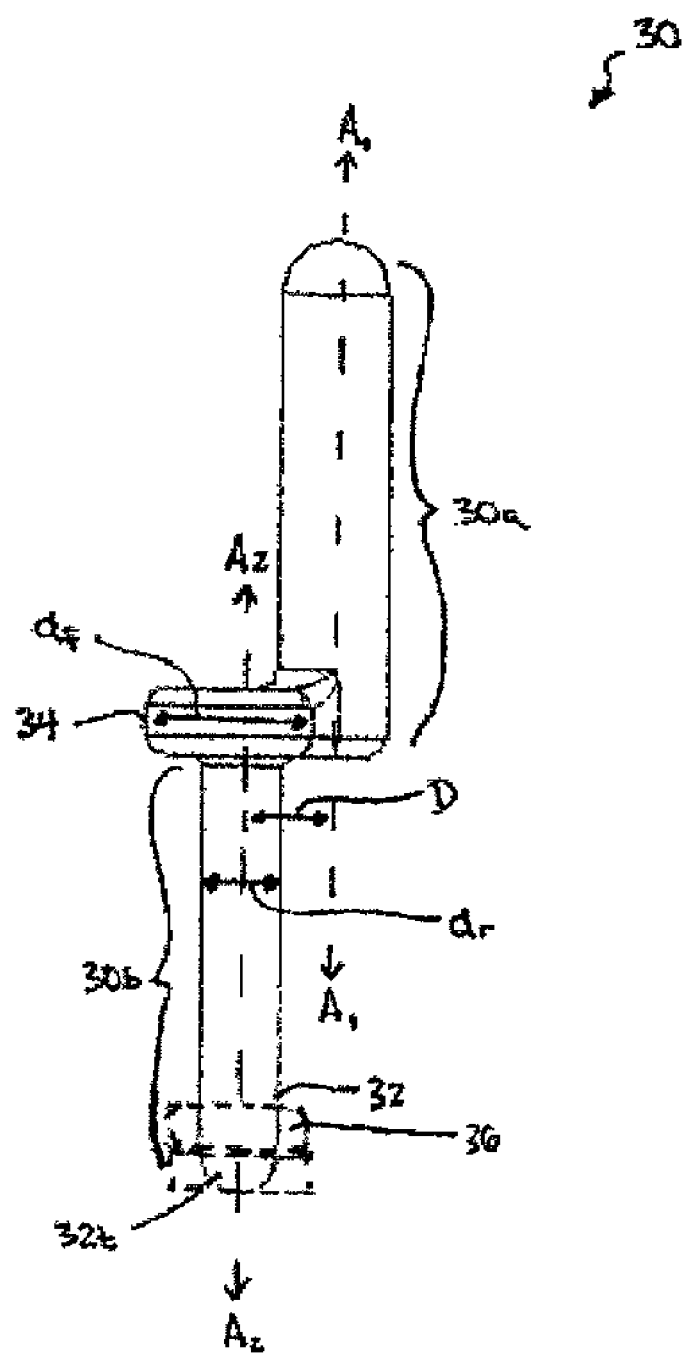
FIG. 3 is a side view of a second member of one of the exemplary implants shown in FIG. 1A.

The second member 30 of the implant 10 can also have a variety of configurations, but in one exemplary embodiment, as shown in more detail in FIG. 3, the second member 30 can have a substantially elongate shape with first and second portions 30a, 30b. The first portion 30a can be adapted to couple to a bone engaging element for mating the first portion 30a to a vertebra, e.g., the superior vertebra 60s, and the second portion 30b can form the extension rod 32 that is adapted to extend through the opening 22i formed in the bearing element 22. The first and second portions 30a, 30b can be coaxial with one another, but in an exemplary embodiment the first and second portions 30a, 30b are axially offset from one another. In particular, the axis $A_1$ of the first portion 30a can be spaced a distance D apart from the axis $A_2$ of the second portion 30b. While the distance can vary, in one exemplary embodiment the distance D can be in the range of about 2 mm to 10 mm. Such a configuration will facilitate positioning of the second portion 30b, e.g., the extension rod 32, relative to the bearing element 22, and it can also allow the extension rod 32 to move relative to the bearing element 22 without abutting against or otherwise coming into contact with the first portion 20a of the first member 20.

As noted above, the first portion 30a of the second member 30 can be adapted to couple to a bone engaging element to mate the first portion 30a to the superior vertebra 60s. Accordingly, the first portion 30a can have a variety of configurations depending on the type of bone engaging element used. In the exemplary embodiment shown in FIGS. 1A and 1B, the bone engaging element is a bone screw 54 having a shank (not shown) that threads into the vertebra 60s, and a U-shaped receiving head 56. Accordingly, the first portion 30a can be in the form of a rod that is adapted to seat within the receiving head 56. A locking element, such as a set screw, can be used to lock the first portion 30a within the receiving head 56, thereby mating the second member 30 to the vertebra 60s. In another exemplary embodiment, the bone screw 54 can be a polyaxial bone screw such that the receiving head 54 is angularly adjustable relative to the shank. Such a configuration will allow the second member 30 to be set at a desired position relative to the first member 20, and in particular the extension rod 32 can be positioned as desired relative to the bearing element 22. The orientation of the second member 30 relative to the first member 20 can be used to control movement of the vertebrae 60s, 60i relative to one another, as will be discussed in more detail below. A person skilled in the art will appreciate that a variety of other devices including, for example, offset connectors, can be used to mate the second member 30 to the vertebra.

The extension rod 32 of the second member 30 can also have a variety of configurations, but it should be adapted to be extend through and slidably move relative to the bearing element 22. In the illustrated exemplary embodiment, the extension rod 32 has a substantially cylindrical shape with a diameter dr that is only slightly less than an inner diameter $d_i$ of the opening formed through the bearing element 22.

The extension rod 32 can also include one or more physical stops formed thereon to limit movement thereof relative to the bearing element 22. While the physical stop(s) can have a variety of shapes and sizes, in the illustrated exemplary embodiment the first portion 30a and the extension rod 32 are separated by a substantially circular flange 34 that forms a physical stop. The flange 34 can be adapted to abut against a superior surface 20s (FIG. 2A) of the first member 20 to limit penetration of the extension rod 32 through the bearing element 22. Accordingly, the flange 34 preferably has an extent, e.g., a diameter $d_f$, that is larger than the diameter $d_i$ of the opening 22i in the bearing element. The terminal end 32t of the extension rod 32 can also include a flange formed thereon, as is further shown in FIG. 3, to prevent removal of the extension rod 32 from the bearing element 22.

The extension rod 32 can also include one or more compressive elements disposed there around and adapted to act as a cushion for preventing hard contact between the extension rod 32 and the bearing element 22, or the second portion 20b of the first member 20. As shown in FIG. 3, the compressive element 36 can be in the form of a donut or similar shaped member that is disposed around the extension rod 32. The compressive element 36 can be positioned adjacent to the flange 34, or it can be disposed or formed on the terminal end 32t of the extension rod 32 as shown. Alternatively, the flange on the terminal end 32t can be formed from a compressive material, or it can include a compressive element mated thereto or formed thereon. A person skilled in the art will appreciate that a variety of techniques can be used to control movement of and limit hard impact between the extension rod 32 and the bearing element 22. A person skilled in the art will also appreciate that a variety of materials can be used to form a compressive element. By way of non-limiting example, suitable materials include polymers, such as polyurethane, silicone-urethane copolymer, polycarbonateurethane. Metallic springs can also be used.

In use, the implant 10 can replace and/or augment one or more of the posterior elements of the spine, including, for example, the facet joints, the lamina, the posterior ligaments, and/or other features of a patient's spinal column. The particular configuration and use of the implant 100 can, however, vary depending on the specific procedure being performed. For example, where a laminectomy is performed and the facet joints are not removed, the implant can be used to reduce the load on the facet joints. Where the facet joints are removed, it may be necessary to add an anti-rotation feature, as will be discussed in more detail below, to prevent rotation of the bone screws relative to the vertebrae. Where the posterior ligaments are removed, it may be desirable to use one or more compressive elements to facilitate control of flexion of the vertebrae. The implant 10 can also be adapted to function with either a natural vertebral disc, or with an artificial disc as previously discussed. Regardless, as noted above, the implant 10 is preferably adapted to allow flexion, extension, and lateral bending of the spine, while substantially restricting posterior-anterior shear and rotation of the spine. While an exemplary method of implanting only one posterior stabilizing implant 10 will be discussed, a person skilled in the art will appreciate that, in an exemplary embodiment, two implants 10, 10' are implanted on opposed lateral sides of adjacent vertebrae. Moreover, any number of implants can be used to couple multiple adjacent vertebrae depending on the needs of the patient.

One exemplary procedure can begin by implanting a bone screw 50 in the inferior vertebra 60i, and implanting a bone screw 54 in the superior vertebra 60s. As shown in FIGS. 1A and 1B, the bone screws 50, 54 are implanted on a lateral side of the vertebrae 60s, 60i to allow another implant 10' to be implanted on the opposed lateral side of the vertebrae 60s, 60i. Once the bone screws 50, 54 are implanted, the first member 20 can be coupled to bone screw 50 by positioning the articulating surface 26 of the first portion 20a on the receiving head such that the central shaft of the bone screw 50 extends through the opening 24 in the first member 20. The locking nut 52 can then be loosely threaded onto the central shaft of the bone screw 50 to loosely attach the first member 20 to the bone screw 50. The first member 20 can then be angularly adjusted as desired, and once properly positioning, the locking nut 52 can be tightened to maintain the first member 20 in a fixed position relative to the vertebra 60i. The second member 30 can be coupled to bone screw 54 by inserting the extension rod 32 through the bearing element 22 and positioning the first portion 30a within the receiving head 56 of the bone screw 54. The locking element, e.g., set screw 58, can then be inserted into the receiving head 56 to loosely mate the second member 30 to the vertebra 60s. Where the bone screw 54 is a polyaxial bone screw, the second member 30 can be angularly adjusted by moving the receiving head 56. Once the second member 30 is properly positioned, the set screw 58 can be fully tightened to maintain the second member 30 in a fixed position relative to the vertebra 60s. A person skilled in the art will appreciate that the bone screws 50, 54 and the first and second members 20, 30 can be implanted and adjusted in any order. In one exemplary embodiment, the second member 30 is positioned as desired and the first member 20 is then positioned as necessary based on the positioning of the second member 30.

While not shown, where the implant 10 is used to replace the facet joints, it may be desirable to include an anti-rotation feature to prevent rotation of the bone screws that are implanted in the superior vertebra 60s. While various anti-rotation techniques can be used, in one embodiment the bone screws can include spikes or other surface protrusions formed on a proximal end of the shank or on the head of the screws to prevent rotation thereof. In another embodiment, a cross-connector can be connected to and extend between the first portion of the second member of each implant, thereby preventing rotation of the bone screw mated thereto.

Once the implant 10 is coupled to the adjacent vertebrae 60s, 60i, the implant 10 can control movement of the vertebrae 60s, 60i relative to one another. In particular, during movement of the spine, the bearing element 22 rotates as the extension rod 32 slidably moves therethrough to control movement of the vertebrae 60s, 60i. Due to the configuration of the implant 10, the bearing element 22 and the extension rod 32 can also substantially prevent axial rotation of the vertebrae 60s, 60i relative to one another, and anterior-posterior shearing can be substantially resisted. FIGS. 4A-4C illustrate the vertebrae 60s, 60i in a neutral position, and during flexion and extension. FIG. 4A illustrates the vertebrae 60s, 60i in a neutral position, 60i. FIG. 4B illustrates the vertebrae 60s, 60i during extension, and as shown the extension rod 32 is fully inserted into the bearing element 22 such that the flange 34 abuts against the bearing element 22. FIG. 4C illustrates flexion of the vertebrae 60s, 60i, and as shown the bearing element 22 is pivoted relative to the first member 20 and the extension rod 32 is substantially withdrawn from the bearing element 22 such that only the terminal end 32t of the extension rod 32 remains in the bearing element 22.

While the extension rod 32 can be positioned to be substantially parallel to the central axis X of the vertebrae 60s, 60i, the extension rod 32 can be positioned at a particular angle relative to the central axis X of the vertebrae 60s, 60i to control the movement of the vertebrae 60s, 60i. As shown in FIG. 4A, the position of the extension rod 32 relative to the vertebrae 60s, 60i is indicated by angle α, which is measured between a line perpendicular to the central axis X and the axis $A_2$ of the extension rod 32. In order to increase flexion, the extension rod 32 can angled toward the central axis of the vertebrae 60s, 60i such that the angle α is less than 90°. At this angle, the flange 34 will be positioned closer to the bearing element 22 in the neutral position. As a result, when the vertebrae 60s, 60i move from the neutral position, shown in FIG. 4A, to the extended position, shown in FIG. 4B, the range of motion will be limited. Conversely, when the vertebrae 60s, 60i move from the neutral position to the flexed position, shown in FIG. 4C, the range of motion will be greater. In order to decrease flexion, the extension rod 32 can angled away from the central axis of the vertebrae 60s, 60i such that the angle α is greater than 90°. At this angle, the flange 34 will be spaced a greater distance apart from the bearing element 22 in the neutral position. As a result, when the vertebrae 60s, 60i move from the neutral position, shown in FIG. 4A, to the extended position, shown in FIG. 4B, the range of motion will be increased. Conversely, when the vertebrae 60s, 60i move from the neutral position to the flexed position, shown in FIG. 4C, the range of motion will be decreased. Accordingly, the angle α of the extension rod 32 can be selected based on the desired range of motion during flexion and extension. A person skilled in the art will appreciate that the angle α can vary depending on the desired result, but in an exemplary embodiment the angle α can be in the range of about 60° to about 120°.

While not shown, the procedure can also include the step of placing a sheath or protective member partially or fully around the implant 10 for preventing tissue from growing on the implant 10 and into the bearing element 22, and for preventing debris from migrating into the spinal canal.

FIGS. 5A-8C illustrate another exemplary embodiment of a posterior stabilizing implant 10. The implant 100 is somewhat similar to implant 10, except that it has a bilateral configuration. In particular, rather than having two implants 10, 10' positioned on opposed lateral sides of two adjacent vertebrae, implant 100 can be positioned along the mid-line of the adjacent vertebrae to control movement of the vertebrae relative to one another.

Figure 5A:
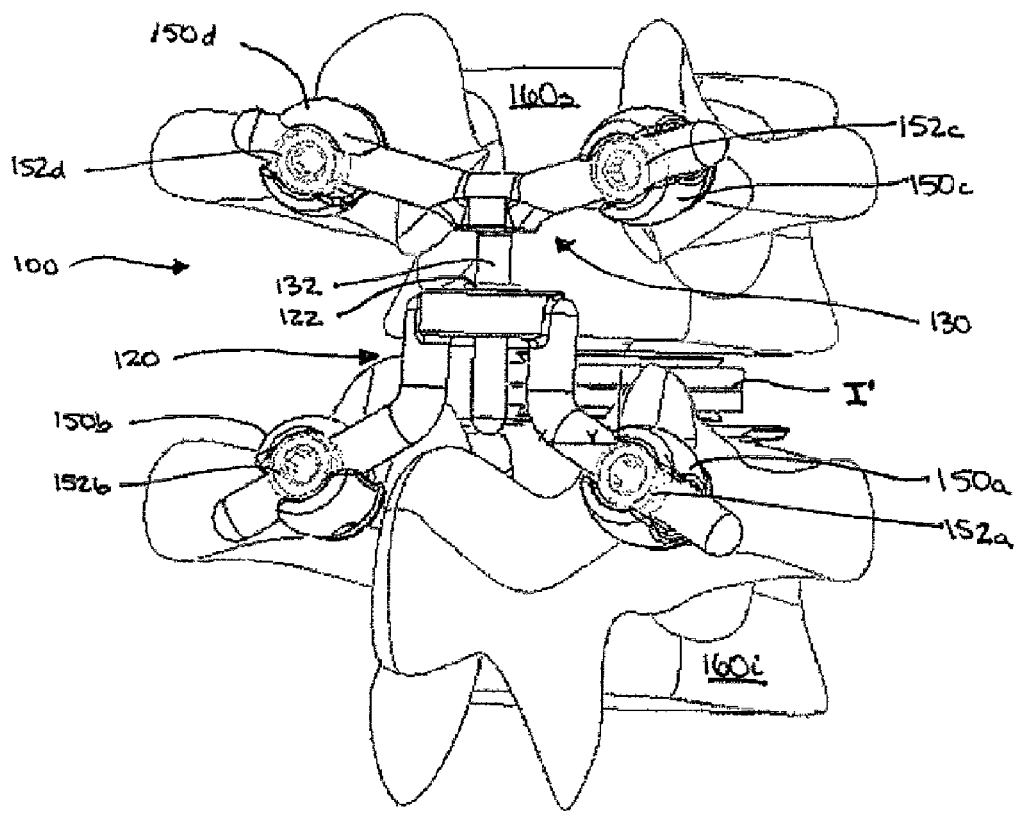
FIG. 5A is a perspective view of another exemplary embodiment of a posterior stabilizing implant coupled to adjacent vertebrae.
Figure 5B:
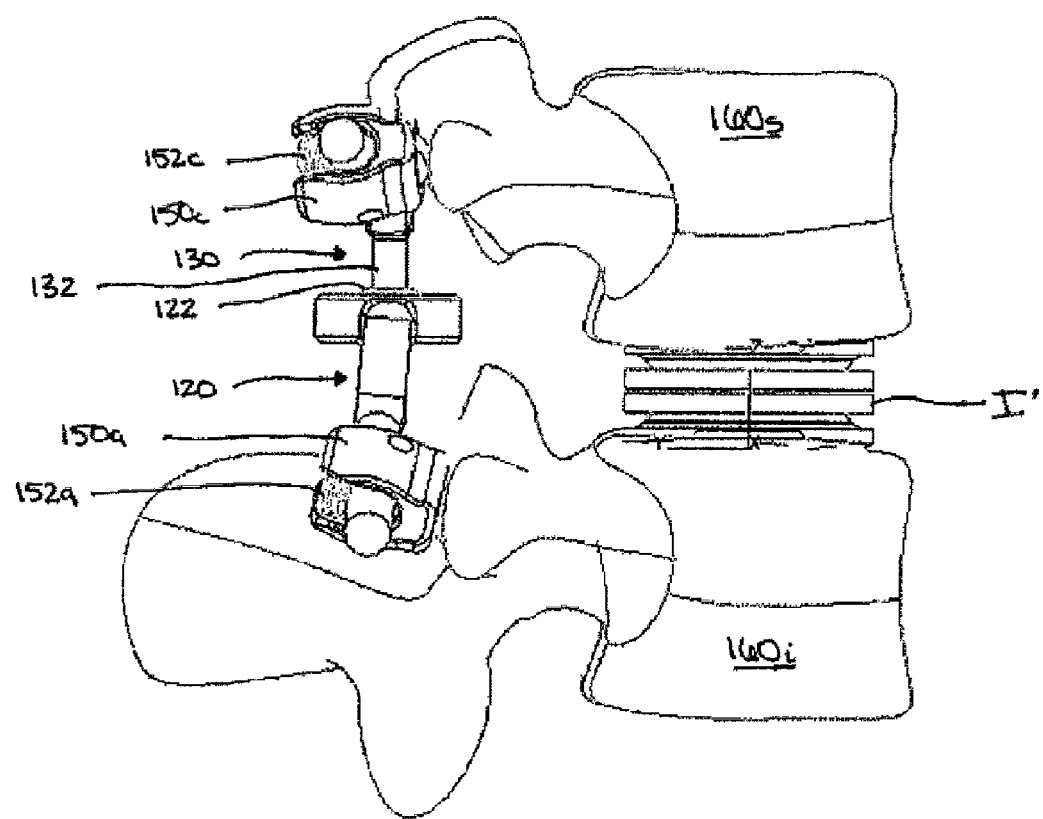
FIG. 5B is a side view of the posterior stabilizing implant shown in FIG. 5A.

As shown in FIGS. 5A and 5B, the exemplary implant 100 generally includes a first member 120 that is adapted to couple to a first vertebra, e.g., an inferior vertebrae 160i, and that includes a bearing element 122 disposed therein, and a second member 130 that is adapted to couple to a second vertebrae, e.g., a superior vertebrae 160s, and that has an extension rod 132 formed thereon. While not shown, the first and second members 120, 130 can be reversed such that the first member 120 is coupled to the superior vertebra 160s and the second member 130 is coupled to the inferior vertebra 160i. In use, the bearing element 122 is adapted to freely rotate relative to the first member 120, and the extension rod 132 is adapted to slidably extend through the bearing element 122 to control movement of the adjacent vertebrae 160s, 160i, allowing flexion, extension, and lateral bending of the spine, while substantially restricting posterior-anterior shear and rotation of the spine. While not shown, the first and second members 120, 130 can be reversed such that the first member 20 is coupled to the superior vertebra 60s and the second member 30 is coupled to the inferior vertebra 60i.

Figure 6:
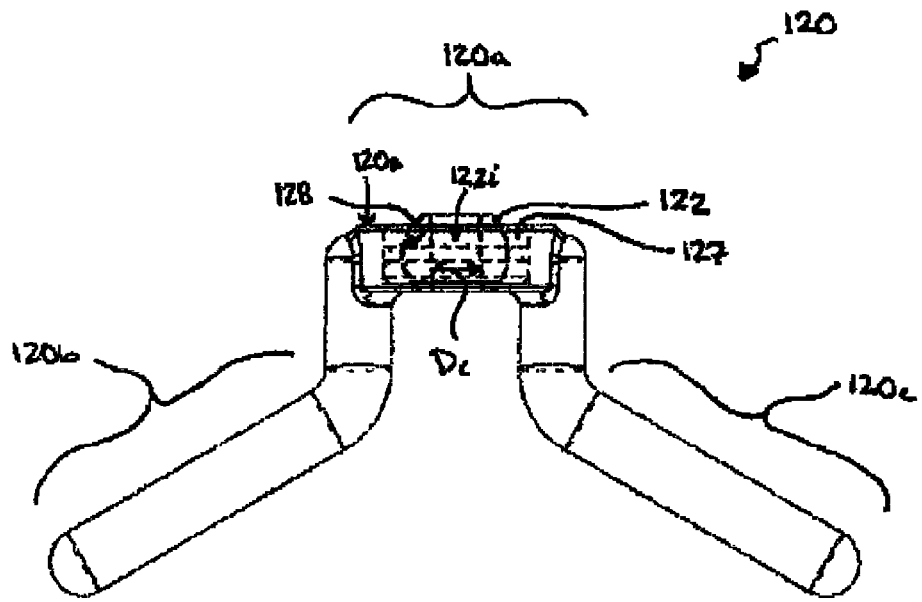
FIG. 6 is a side view of a first member of the exemplary implant shown in FIG. 5A.

The first member 120 of the implant 100, which is shown in more detail in FIG. 6, can have a variety of configurations. In the illustrated exemplary embodiment, however, the first member 120 is substantially Y-shaped and it includes a central portion 120a having the bearing element 122 disposed therein, and first and second arms 120b, 120c that extend from the central portion 120a and that are adapted to mate to a vertebra, e.g., the inferior vertebra 60i. The central portion 120a and the first and second arms 120b, 120c can have a variety of shapes and sizes, and the configuration can vary depending on the intended use. In the illustrated exemplary embodiment, the central portion 120a has a substantially planar cylindrical configuration such that it is adapted to seat the bearing element 122 therein, and the first and second arms 120b, 120c each extend distally and laterally outward from the central portion 120a. Such a configuration allows the first and second arms 120b, 120c to mate to opposed lateral sides of the vertebra 160i.

The first and second arms 120b, 120c can mate to the inferior vertebra 160i using a variety of techniques. In the illustrated exemplary embodiment, the arms 120b, 120c are in the form of rods having a generally elongate, substantially cylindrical configuration. This allows each arm 120b, 120c to be received within a receiving head of a bone engaging element. In the embodiment shown in FIGS. 5A and 5B, the bone engaging elements are bone screws 150a, 150b that are implanted on opposed lateral sides of the inferior vertebra 160i. As previously described above with respect to FIGS. 1A and 1B, the bone screws 150a, 150b can include a U-shaped head that is adapted to seat an arm 120b, 120c, and a locking element, such as a set screw 152a, 152b can be used to lock the arms 120b, 120c to the bone screws 150a, 150b. The receiving head of each bone screw 150a, 150b can also be polyaxially movable relative to the threaded shank (not shown) of the bone screw 150a, 150b to allow the first member 120 to be angularly adjustable relative to the vertebra 160i. Such a configuration allows the bearing element 122 to be positioned as desired, as will be discussed in more detail below.

As noted above, the first member 120 also includes a bearing element 122 disposed therein. The bearing element 122 can have a configuration that is the same as or similar to the configuration previously described with respect to bearing element 22 shown in FIGS. 1A-2. In particular, the bearing element 122 can be freely rotatably disposed within a spherical recess formed in the central portion 120a of the first member 120, or it can be freely rotatably disposed within an insert 127 that is disposed within the central portion 120a of the first member 120, as shown in FIG. 6. As was also previously described, the bearing element 122 can be a standard ball bearing that includes an opening 122i formed therethrough for slidably receiving the extension rod 132 on the second member 130. The bearing element 122, the recess 128 formed within the insert 127 for seating the bearing element 122, and/or the opening 122i formed through the bearing element 122 can also include a coating to reduce friction and reduce wear.

Figure 7:
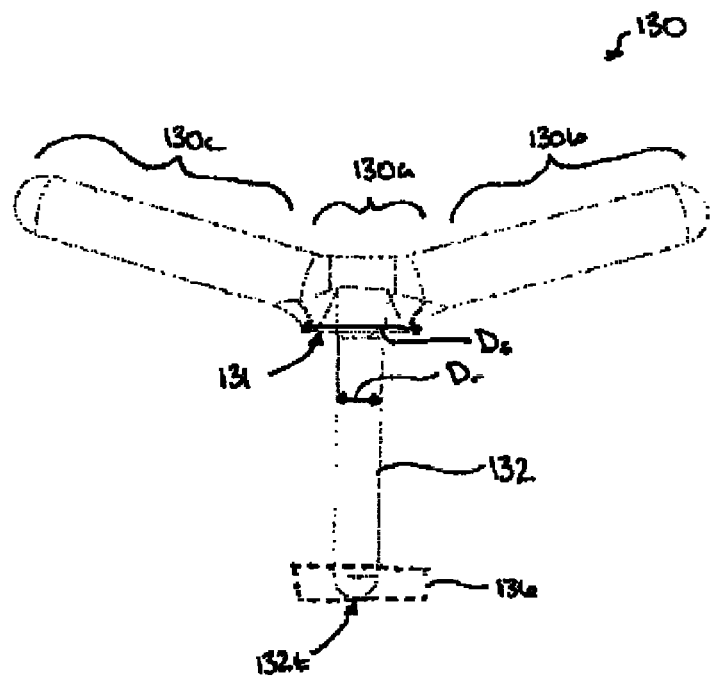
FIG. 7 is a side view of a second member of the exemplary implant shown in FIG. 5A.

The second member 130 of the implant 10 can also have a variety of configurations, but in an exemplary embodiment, as shown in more detail in FIG. 7, the second member 130 can be substantially Y-shaped with a central portion 130a having first and second arms 130b, 130c extending laterally from opposed sides thereof. The extension rod 132 can also extend from the central portion 130a. The particular angle of each arms 130b, 130c relative to the extension rod 132 can vary depending on the intended use, but in an exemplary embodiment 130b, 130c that arms have a configuration that allows each arm 130b, 130c to mate to opposed lateral sides of a vertebra, e.g., the superior vertebra 160s.

Each arm 130b, 130c can be mated to the vertebra 160s using a variety of techniques, however in an exemplary embodiment each arm 130b, 130c is in the form of a rod having a substantially elongate cylindrical shape such that the arms 130b, 130c can mate to a receiving head of a bone engaging element, such as bone screws 150c and 150d as shown. As previously described, the bone screws 150c, 150d can be polyaxial bone screws to allow the position of the second member 130 to be angularly adjusted as desired, and in particular to allow the extension rod 132 to be positioned as desired relative to the bearing element 122. A locking element, such as a set screw 152c, 152d can be used to lock the arms 130b, 130c to the bone screws 150c, 150d.

The extension rod 132 of the second member 130 can also have a variety of configurations, but in an exemplary embodiment the extension rod 132 is similar to extension rod 22 previously described with respect to FIGS. 1A, 1B, and 3. In particular, the extension rod 132 should be adapted to be extend through and slidably move relative to the bearing element 122. In the illustrated exemplary embodiment, the extension rod 132 has a substantially cylindrical shape with a diameter $D_r$ that is only slightly less than an inner diameter $D_i$ of the opening formed through the bearing element 122.

As previously described with respect to FIG. 3, the extension rod 132 can also include a physical stop formed thereon to limit movement thereof relative to the bearing element 122. While the physical stop can have a variety of shapes and sizes, in the illustrated exemplary embodiment the central portion 130a has a substantially cylindrical shape with a surface 131 that is adapted to abut against the bearing element 122 to limit penetration of the extension rod 132 through the bearing element 122. Accordingly, the surface 131 preferably has an extent, e.g., a diameter $D_p$ that is larger than the diameter $D_i$ of the opening 122i in the bearing element.

The extension rod 132 can also include one or more compressive elements disposed there around, as previously described with respect to FIG. 3, for providing a cushion to substantially prevent hard contact between the extension rod 132 and the bearing element 122, or the central portion 120a of the first member 120. The compressive element(s) (not shown) can be in the form of a donut or similar shaped member that is disposed around the extension rod 132. The compressive element can be positioned adjacent to surface 131, and/or it can be disposed or formed on the terminal end 132t of the extension rod 132. The terminal end 132t can also include a stop surface or flange 136 formed thereon, as shown in phantom in FIG. 7, to prevent the extension rod 132 from being fully withdrawn from the bearing element 122, and optionally to retain a compressive element on the extension rod 132. Alternatively, flange 136 can be formed from a compressive material, or it can include a compressive element mated thereto or formed thereon. A person skilled in the art will appreciate that a variety of techniques can be used to control movement of and limit hard impact between the extension rod 132 and the bearing element 122. A person skilled in the art will also appreciate that a variety of materials can be used to form a compressive element.

While not shown, in another exemplary embodiment the extension rod 132 can be adjustable relative to the first and second arms 130b, 130c. For example, the extension rod 132 can be rotatably mated to the central portion 130a, and the central portion 130a can include a locking mechanism that is adapted to lock the extension rod 132 in a desired fixed position. Such a configuration is particularly desirable where the bone screws 150c, 150d used to attach the arms 130b, 130c to the vertebra 160s are not polyaxial. The extension rod 132 can thus be positioned at a desired angle relative to the vertebra 160s, and then locked in place to maintain it at the desired angular position. A person skilled in the art will appreciate that a variety of other techniques can be used to allow the extension rod 132 to be adjusted relative to the remainder of the second member 130.

In use, the implant 100 can replace and/or augment one or more of the posterior elements of the spine, including, for example, the facet joints, the lamina, the posterior ligaments, and/or other features of a patient's spinal column. The implant 100 can also be adapted to function with either a natural vertebral disc, or with an artificial disc as previously discussed. Regardless, as noted above, the implant 100 is preferably adapted to allow flexion, extension, and lateral bending of the spine, while substantially restricting posterior-anterior shear and rotation of the spine. The particular configuration and use of the implant 100 can, however, vary depending on the specific procedure being performed. For example, where a laminectomy is performed and the facet joints are not removed, the implant can be used to reduce the load on the facet joints. Where the facet joints are removed, it may be necessary to add an anti-rotation feature as previously discussed to prevent rotation of the bone screws relative to the vertebrae. Where the posterior ligaments are removed, it may be desirable to use one or more compressive elements to facilitate control of flexion of the vertebrae.

One exemplary procedure can begin by implanting two bone screws 150a, 150b in the inferior vertebra 160i, and implanting two bone screws 150c, 150d in the superior vertebra 160s. As shown in FIGS. 5A and 5B, the bone screws 150a, 150b, 150c, 150d are implanted on opposed lateral sides of the vertebrae 160s, 160i. Once the bone screws 150a, 150b, 150c, 150d are implanted, the first member 120 can be coupled to bone screws 150a, 150b by positioning the arms 120b, 120c in the receiving head of the bone screws 150a, 150b such that the central portion 120a is positioned toward the superior vertebra 160s. The set screws 152a, 152b can then be loosely threaded onto the receiving heads of the bone screws 150a, 150b to loosely attach the first member 120 to the bone screws 150a, 150b. Where the bone screws 150a, 150b are polyaxial bone screws, the first member 120 can be angularly adjusted by moving the receiving heads of the screws 150a, 150b. Once properly positioned, the set screws 152a, 150s can be tightened to maintain the first member 120 in a fixed position relative to the vertebra 160i. As previously described, the extension rod 132 can be positioned at a desired angle relative to the vertebrae 160s, 160i. The second member 130 can similarly be coupled to two bone screws 150c, 150d by inserting the extension rod 132 through the bearing element 122, and positioning the arms 130b, 130c within the receiving heads of the bone screws 150c, 150d. The set screws 152c, 152d can be loosely mated to the receiving heads to retain the arms 130b, 130c therein. Where the bone screws 150c, 150d are polyaxial bone screws, the second member 130 can be angularly adjusted by moving the receiving heads of the screws 150c, 150d. Once the second member 130 is properly positioned, the set screws 152c, 152d can be fully tightened to maintain the second member 130 in a fixed position relative to the vertebra 160s. A person skilled in the art will appreciate that the bone screws 150a, 150b, 150c, 150d and the first and second members 120, 130 can be implanted and adjusted in any order. In one exemplary embodiment, the second member 130 is positioned as desired and the first member 120 is then positioned as necessary based on the positioning of the second member 130.

Once the implant 100 is coupled to the adjacent vertebrae 160s, 160i, the implant 100 can control movement of the vertebrae 160s, 160i relative to one another. In particular, during movement of the spine, the bearing element 122 rotates as the extension rod 132 slidably moves therethrough to control movement of the vertebrae 160s, 160i. Due to the configuration of the implant 100, the bearing element 122 and the extension rod 132 can also substantially prevent axial rotation of the vertebrae 160s, 160i relative to one another, and anterior-posterior shearing can be substantially resisted. FIGS. 8A-8C illustrate the vertebrae 160s, 160i in a neutral position, and during flexion and extension. FIG. 8A illustrates the vertebrae 160s, 160i in a neutral position, and as shown the extension rod 132 is substantially parallel to the central axis Y of the vertebrae 160s, 160i. FIG. 8B illustrates the vertebrae 160s, 160i during extension, and as shown the extension rod 132 is fully inserted into the bearing element 122 such that surface 131 abuts against the bearing element 122. FIG. 8C illustrates flexion of the vertebrae 160s, 160i, and as shown the bearing element 122 is pivoted relative to the first member 120 and the extension rod 132 is substantially withdrawn from the bearing element 122 such that only the terminal end 132t of the extension rod 132 remains in the bearing element 122.

While not shown, the procedure can also include the step of placing a sheath or protective member partially or fully around the implant 100 for preventing tissue from growing on the implant 100 and into the bearing element 122, and for preventing debris from migrating into the spinal canal.

Figure 9A:
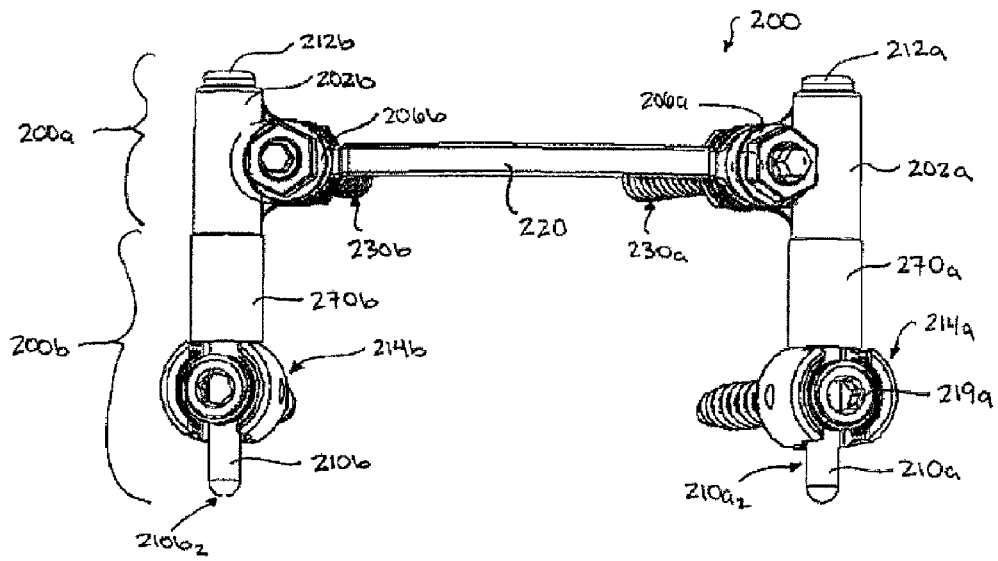
FIG. 9A is a posterior view of another embodiment of a posterior stabilizing implant having opposed lateral members that are connected to one another.
Figure 9B:
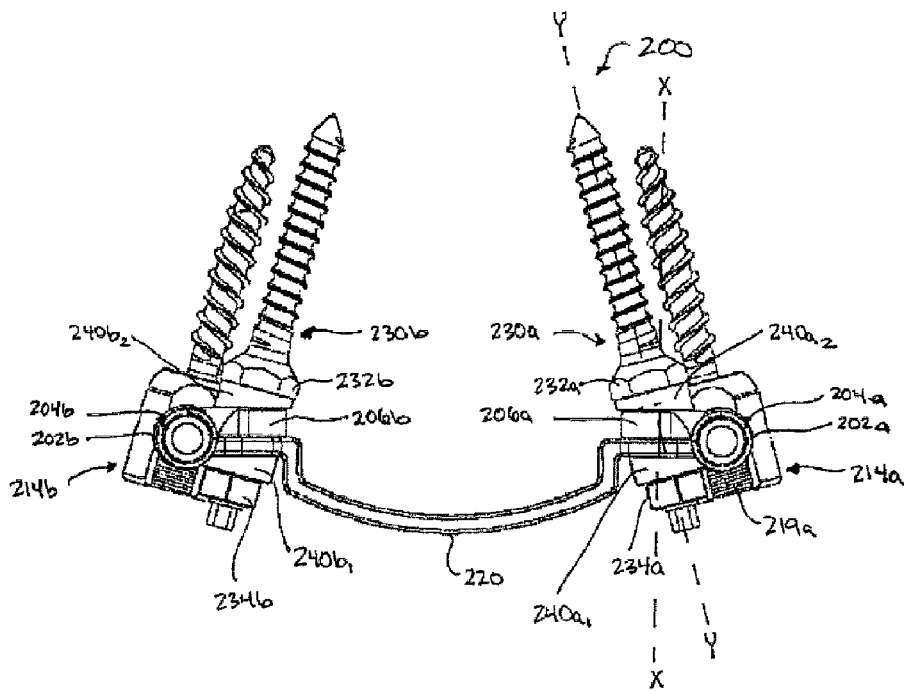
FIG. 9B is a top view of the posterior stabilizing implant shown in FIG. 9A.

FIGS. 9A-9B illustrate yet another exemplary embodiment of a posterior stabilizing implant 200. In this embodiment, rather than having a bearing element that allows pivotal movement between two components, the implant 200 includes a bearing element that allows linear movement of two components. In particular, as shown, the implant 200 can include a first member 200a that is adapted to couple to a first vertebra, and a second member 200b that is adapted to couple to a second vertebra and to slidably move relative to the first member 200a to allow or control extension, flexion, and lateral bending of the adjacent vertebrae, preferably while substantially limiting or preventing axial rotation and shearing. In an exemplary embodiment, one of the first and second members 200a, 200b can be configured to rigidly couple to a vertebra, and the other one of the members 200a, 200b can be configured to dynamically couple to a vertebra, thereby allowing linear movement between the two components.

The first member 200a can have a variety of configurations, but in the illustrated exemplary embodiment it includes opposed first and second lateral members 202a, 202b that are adapted to be coupled to opposed lateral sides of a vertebra. The first member 200a can also include a connecting member 220 that extends between and connects to the first and second lateral members 202a, 202b. The connecting member 220 will be discussed in more detail below with respect to FIG. 11. Each lateral member 202a, 202b can have a variety of configurations, but in one exemplary embodiment each lateral member 202a, 202b is adapted to slidably receive a portion of the second member 200b to allow linear movement between the first and second members 200a, 200b. While this can be achieved using various techniques, in the illustrated exemplary embodiment each lateral member 202a, 202b is in the form of a cylindrical member having an inner lumen 204a, 204b (FIG. 9B) extending therethrough. Since each lateral member 202a, 202b preferably has substantially the same configuration, only one lateral member, e.g., the first lateral member 202a, will be described in detail with reference to FIGS. 10A and 10B. As shown, the first lateral member 202a has a lumen 204a formed therethrough. The inner lumen 204a can vary in shape and size, but in one exemplary embodiment the inner lumen 204a includes a first portion $204a_1$ having a diameter $d_1$ that is greater than a diameter $d_2$ of a second portion $204a_2$ of the lumen 204a. The enlarged diameter portion $204a_1$ allows the lateral member 202a to receive a head 212a, 212b of a sliding pin 210a, 210b of the second member 200b, which will be discussed in more detail below. The enlarged diameter portion $204a_1$ also provides a shelf 205 formed within the inner lumen 204a that can function as a stop surface to receive the head 212a, 212b of the sliding pin 210a, 210b. Although not shown, a spring or other compressive element could rest between shelf 205 and sliding pin 210a in order to provide some resistance to flexion. A person skilled in the art will appreciate that a variety of other techniques can be used to limit movement of the sliding pins 210a, 210b with respect to the lateral members 202a, 202b, certain exemplary embodiments of which will be discussed in more detail below.

Figure 10A:
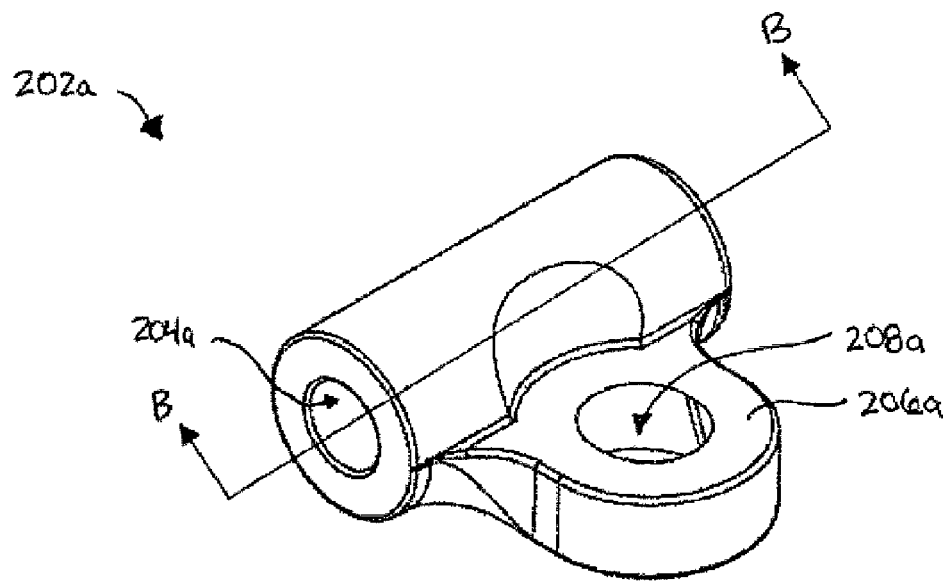
FIG. 10A is a perspective view of one exemplary embodiment of one of the lateral connectors of the posterior stabilizing implant shown in FIGS. 9A and 9B.
Figure 10B:
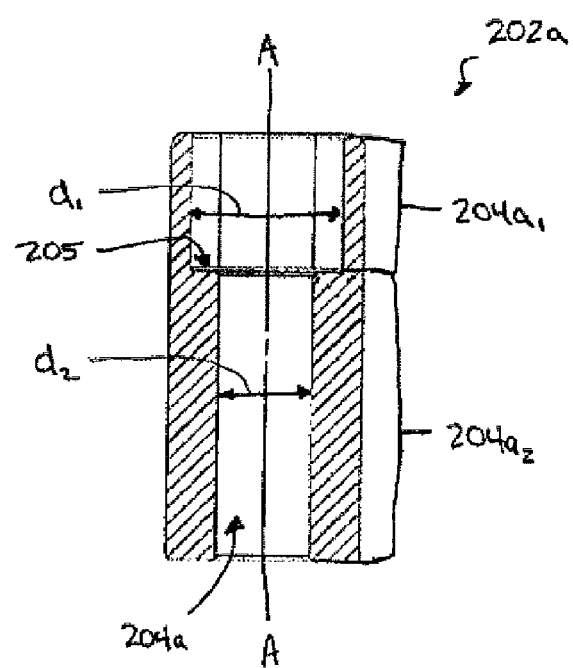
FIG. 10B is a cross-sectional view of the lateral connector shown in FIG. 10A taken across line B-B.
Figure 12:
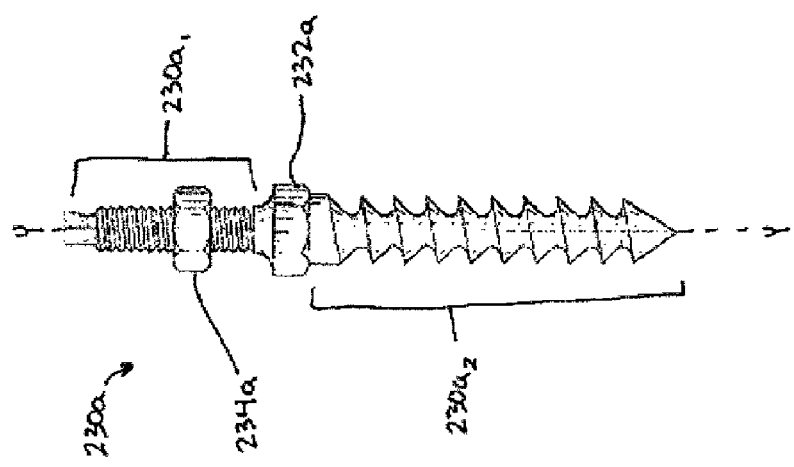
FIG. 12 is a perspective view of one exemplary embodiment of a bone screw for mating the posterior stabilizing implant shown in FIGS. 9A and 9B to a vertebra.

Each lateral member 202a, 202b can also include an offset connector 206a, 206b formed thereon to facilitate mating thereof to the connecting member 220, and to allow the first and second lateral members 202a, 202b to be mated to a vertebra. The offset connectors 206a, 206b can have a variety of configurations, but in one exemplary embodiment the connectors 206a, 206b are the same or substantially similar. Accordingly, only one of the offset connectors 206a, 206b, e.g., the offset connector 206a on the first lateral member 202a, will be described in detail. Referring to FIG. 10A, the exemplary offset connector 206a is substantially planar and extends outward from the cylindrical portion of the lateral member 202a. The offset connector 206a can also include a thru-bore 208a formed therein for receiving a fastening element, such as a bone screw, for mating the offset connector 206a, as well as the connecting member 220, to a vertebra. Exemplary techniques for mating the offset connectors 206a, 206b to bone and to the connecting member 220 will be described in more detail with respect to FIGS. 12-14.

Figure 11:
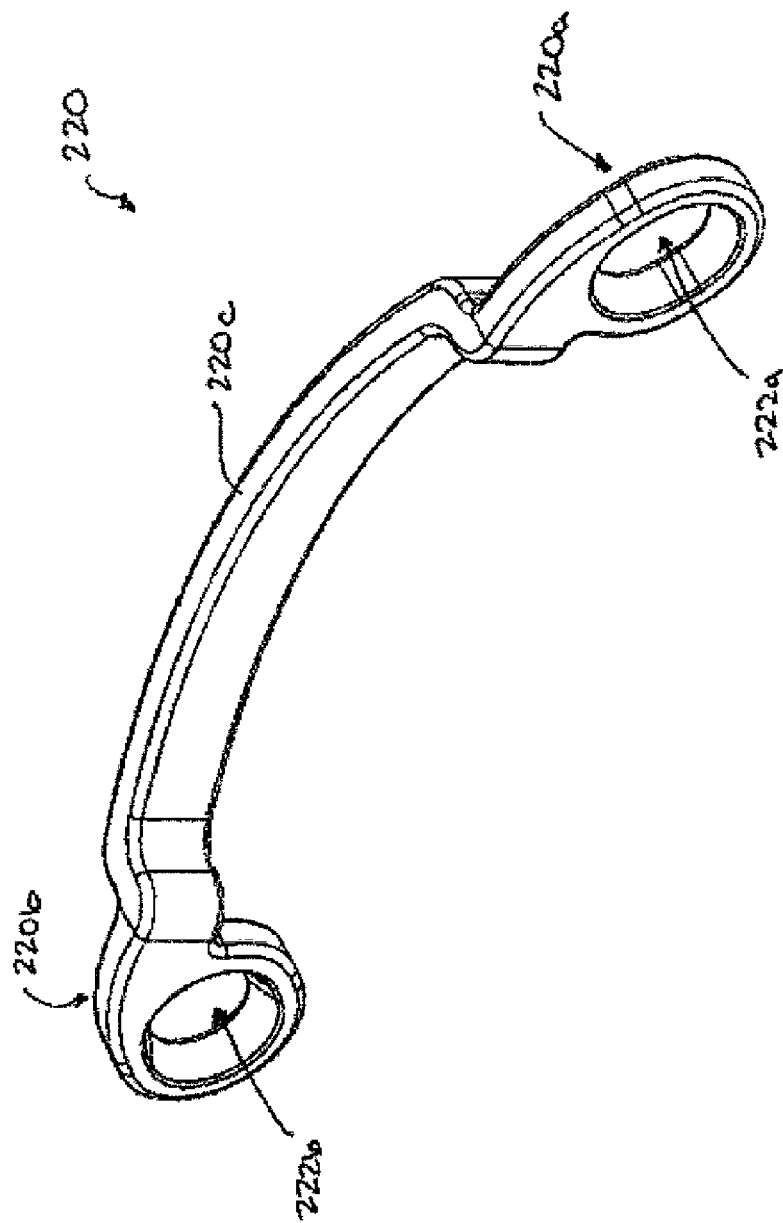
FIG. 11 is a perspective view of one exemplary embodiment of a connecting member of the posterior stabilizing implant shown in FIGS. 9A and 9B.

The connecting member 220 can also have a variety of configurations, but as indicated above it is preferably adapted to extend between and couple to the first and second lateral members 202a, 202b. The connecting member 220, while not necessary, is particularly advantageous in that it can provide a rigid connection between the first and second lateral members 202a, 202b, thereby preventing rotation of the screw relative to the bone. FIG. 11 illustrates exemplary connecting member 220 in more detail, and as shown the connecting member 220 is in the form of an elongate substantially planar rod. The shape of the connecting member 220 can vary, but in an exemplary embodiment the connecting member 220 has a shape that is adapted to ensure clearance of the facet joints and the spinous processes of the adjacent vertebrae when the connecting member 220 is mated to the first and second lateral members 202a, 202b. As shown in FIG. 11, the connecting member 220 includes a central portion 220c that is substantially curved, and opposed ends 220a, 220b each having a planar configuration. While not shown, the opposed ends 220a, 220b could alternatively be polyaxially connected to the central portion 220c to allow for independent alignment of each end 220a, 220b. Each end 220a, 220b can have a thru-bore 222a, 22b formed therein for receiving a fastening element for mating the connecting member 220 to the first and second lateral members 202a, 202b and to bone. A person skilled in the art will appreciate that the connecting member 220 can have a variety of other configurations, and that the configuration can vary depending on the intended use.

As indicated above, a variety of techniques can be used to mate the connecting member 220 to the lateral members 202a, 202b. In an exemplary embodiment, as shown in FIGS. 9A and 9B, the connecting member 220 is mated to the first and second lateral members 202a, 202b using fastening elements, such as first and second bone screws 230a, 230b. One of the bone screws, e.g., the first bone screw 230a is shown in detail in FIG. 12. As shown, the bone screw 230a has a proximal portion $230a_1$ with threads formed thereon, a distal bone-engaging portion $230a_2$, and a flange 232a separating the proximal and distal portions $230a_1$, $230a_2$. The proximal portion $230a_1$ is adapted to extend through the thru-bore 208a formed in the offset connector 206a of the first lateral member 202a, and through the thru-bore 222a formed in the connecting member 220. A locking mechanism, such as a locking nut 234a, can then be threaded onto the proximal portion $230a_1$ of the bone screw 230a to mate the connecting member 220 and the first lateral member 202a to one another and to a first vertebra.

Figure 13:
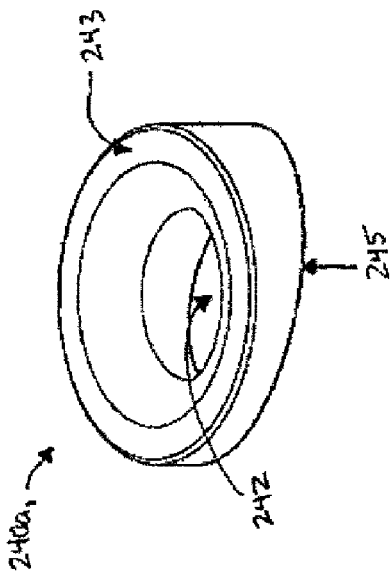
FIG. 13 is a perspective view of one exemplary embodiment of a washer of the posterior stabilizing implant shown in FIGS. 9A and 9B.

In certain exemplary embodiments, an axis Y of the bone screw 230a can be adapted to be positioned at an angle relative to an axis X of the thru-bore 222b in the connecting member 220 and the thru-bore 208a in the offset connector 206a of the first lateral member 202a, as shown in FIG. 9B. Furthermore, the axis Y of the bone screw 230a can be adapted to be positioned at an angle relative to an axis of the sliding pins 210a, 210b. While various techniques can be used to allow angular variations between the bone screws 230a, 230b and the connecting member 220 and the lateral members 202a, 202b, in one exemplary embodiment, one or more washers can be used to provide an angular connection. As shown in FIG. 9B, each lateral member 202a, 202b of the implant 200 includes a first washer $240a_1$, $240b_1$ disposed between the terminal end 220a, 220b of the connecting member 220 and the locking nut 234a, 234b, and a second washer $240a_2$, $240b_2$ disposed between the flange 232a, 232b formed on the bone screw 230a, 230b and the terminal end 220a, 220b of the connecting member 220. Each washer $240a_1$, $240b_1$, $240a_2$, $240b_2$ can have a variety of configurations, but in an exemplary embodiment all four washers $240a_1$, $240b_1$, $240a_2$, $240b_2$ are substantially identical. Accordingly, only one of the washers, e.g., washer $240a_1$, will be described in detail. Referring to FIG. 13, as shown the washer $240a_1$ is substantially cylindrical with a bore 242a formed therethrough. In an exemplary embodiment, the washer $240a_1$ has an angular configuration such that a first surface 243 of the washer $240a_1$ is positioned at an angle relative to a second opposed surface 245 of the washer $240a_1$. The bore 242a in the washer $240a_1$ can also taper to allow further angular variations between the connecting member 220 and the lateral member 202a and the axis Y of the bone screw 230a. In use, referring back to FIG. 9B, the bone screws 230a, 230b can be implanted in the vertebra at a desired angle, and the washers $240a_1$, $240b_1$, $240a_2$, $240b_2$ allow the lateral members 202a, 202b and the connecting member 220 to be mated thereto at a desired orientation regardless of the particular angle of the bone screws 230a, 230b.

Figure 14:
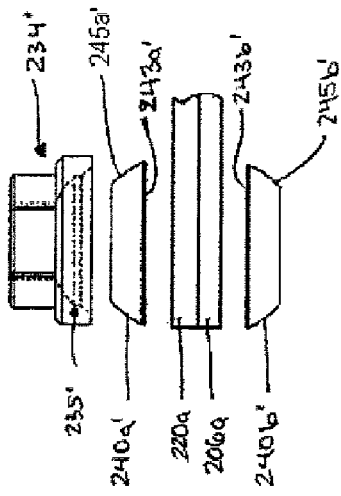
FIG. 14 is a perspective view of another exemplary embodiment of a washer for use with a posterior stabilizing implant.

FIG. 14 illustrates yet another embodiment of a technique for allowing angular variations between the bone screws 230a, 230b and the connecting member 220 and the lateral members 202a, 202b. In this embodiment, which illustrates only one assembly for use with, for example, the first lateral member 202a and the first terminal end 206a of the connecting member 220, two washers 240a', 240b' are provided. Each washer 240a', 240b' has a planar surface 243a', 243b' and an opposed spherical surface 245a', 245b'. The planar surface 243a' of the first washer 240a' can be positioned adjacent to the terminal end 220a of the connecting member 220, and the planar surface 243b' of the second washer 240b' can be positioned adjacent to the offset connector 206a of the first lateral member 202a. The opposed spherical surfaces 245a', 245b' of the washers 240a', 240b' allow the bone screw 230a to be disposed through the washers 240a', 240b', the terminal end 220a of the connecting member 220, and the offset connector 206a at an angle. A locking nut 234' having a spherical cavity 235' formed therein can be mated to the proximal portion 230a$_1$ of the bone screw 230a. The spherical cavity 235' allows the locking nut 234' to pivot about the spherical surface 245a' of the first washer 240a', thus allowing the locking nut 234' to mate to the angularly oriented bone screw 230a. A person skilled in the art will appreciate that a variety of other techniques can be used to mate the bone screws or other fastening elements to the connecting member and the lateral members.

Figure 15:
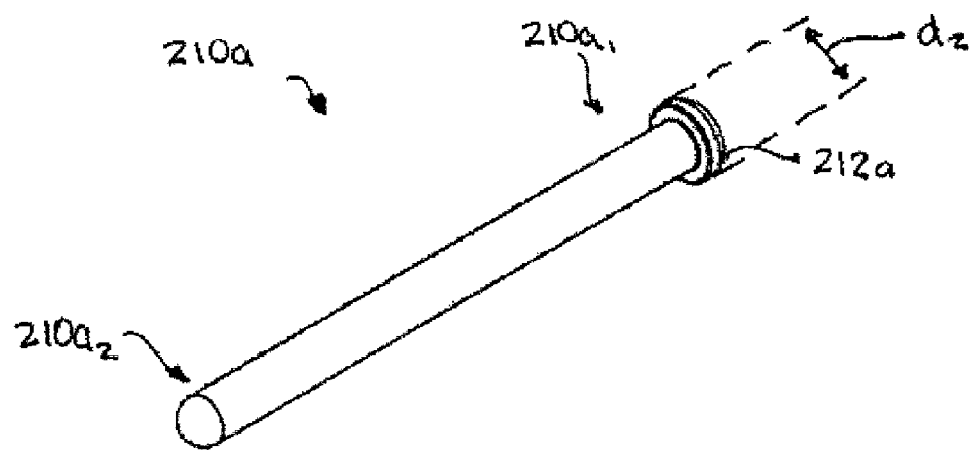
FIG. 15 is a perspective view of one exemplary embodiment of one of the sliding pins shown in FIGS. 9A and 9B.

Referring back to FIGS. 9A and 9B, the implant 200 can also include a second member 200b that is adapted to couple to a second vertebra and to move relative to the first member 200a to control movement of the adjacent vertebrae. While the second member 200b can have a variety of configurations, in the exemplary embodiment shown in FIGS. 9A and 9B the second member 200b includes first and second sliding pins 210a, 210b that are adapted to be slidably disposed through the lumens 204a, 204b in the first and second lateral members 202a, 202b, respectively. In an exemplary embodiment, the first and second sliding pins 210a, 210b are the same or substantially identical, and thus only one pin, e.g., the first sliding pin 210a, will be described in detail. Referring to FIG. 15, the first sliding pin 210a has a generally elongate rod-like shape with a head 212a formed on a first terminal end 210a$_1$ thereof. As previously discussed, the head 212a can be adapted to be received with the enlarged diameter region 204a$_1$ of the lumen 204a in the first lateral member 202a to allow sliding movement of the sliding pin 210a with respect to the first lateral member 202a. In an exemplary embodiment, the head 212a has a diameter d$_3$ that is less than the diameter d$_1$ of the enlarged diameter portion 204a$_1$, but that is greater than the diameter d$_2$ of the second portion 204a$_2$ of the lumen 204a in the first lateral member 202a. Thus, in use, the head 212a is allowed to slide into the first portion 204a$_1$ of the lumen 204a in the first lateral member 202a until it abuts against the shelf 205, at which point further movement is prevented. A person skilled in the art will appreciate that the components of the second member 200b can have a variety of other configurations.

As previously noted, the second member 200b can be adapted to couple to a second vertebra. Thus, in an exemplary embodiment, the second member 200b can also include first and second fastening elements 214a, 214b for coupling a second terminal end 210a$_1$, 210a$_2$ of each sliding pin 210a, 210b to a vertebra. While the fastening elements 214a, 214b can be configured to provide a rigid connection between the sliding pins 210a, 210b and a vertebra, in an exemplary embodiment each fastening element 214a, 214b is configured to provide a dynamic connection between the sliding pins 210a, 210b and the second vertebra. This can be achieved using a variety of techniques.

Figure 16:
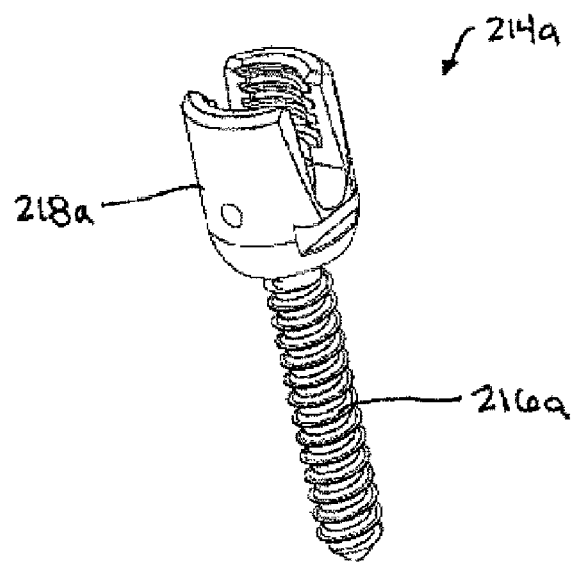
FIG. 16 is a perspective view of a prior art polyaxial bone screw for coupling the sliding pin shown in FIG. 15 to bone.

In the embodiment shown in FIGS. 9A and 9B, first and second polyaxial bone screws 214a, 214b are used to provide a dynamic connection between the first and second sliding pins 210a, 210b and a vertebra mated thereto. The first polyaxial bone screw 214a is shown in more detail in FIG. 16, and as shown it includes a threaded shank 216a having a receiving head 218a formed thereon and pivotally coupled to the shank 216a to provide polyaxial movement of the head 218a relative to the shank 216a. One of the sliding pins, e.g., the terminal end 210a$_2$ of the first sliding pin 210a, can be disposed within 1 the receiving head 218a and a locking mechanism, such as a set screw 219a (FIGS. 9A-9B), can be mated to the head 218a to lock the sliding pin 210a therein. While the pin 210a is locked with respect to the head 218a, the head 218a is free to pivotally or polyaxially move about the shaft 216a, thereby allowing dynamic movement of the second member 200b of the posterior stabilizing implant 200. A person skilled in the art will appreciate that a variety of other techniques can be used to provide a dynamic mating connection between the sliding pins 210a, 210b and a vertebra. Moreover, while the second member 200b is shown having a dynamic connection, the second member 200b can be rigidly mated to the second vertebra, and the first member 200a can by dynamically mated to the first vertebra.

Figure 17B:
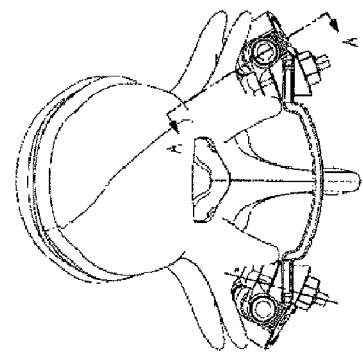
FIG. 17B is a top view of the posterior stabilizing implant shown in FIG. 17A.
Figure 17D:
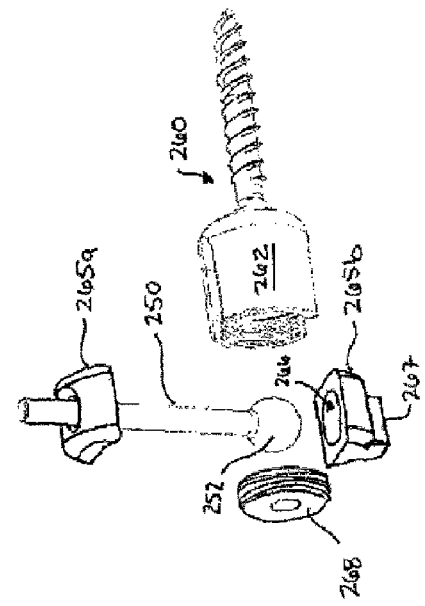
FIG. 17D is an exploded view of a portion of the posterior stabilizing implant shown in FIGS. 17A-17C.
Figure 17A:
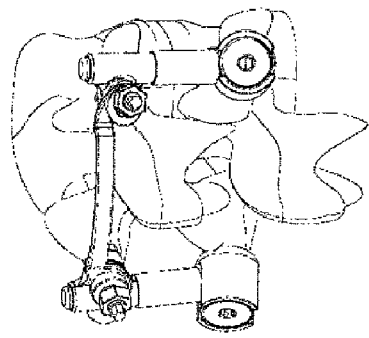
FIG. 17A is a perspective posterior view of another exemplary embodiment of a posterior stabilizing implant coupled to adjacent vertebrae.
Figure 17C:
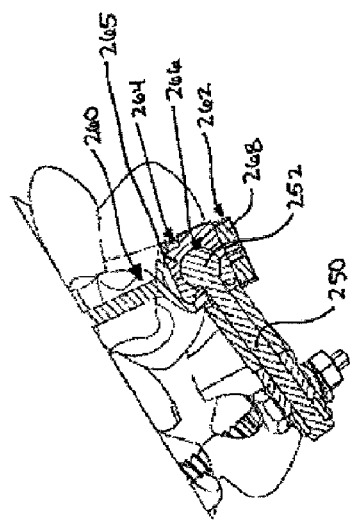
FIG. 17C is a cross-sectional view of the posterior stabilizing implant shown in FIG. 17B taken across line A-A.

FIGS. 17A-17D illustrate another embodiment of a technique for dynamically mating the sliding pins of the second member to a vertebra. In the embodiment shown in FIGS. 17A-17D, rather than having a polyaxial bone screw, the second terminal end of the sliding pin member can include a spherical head formed thereon. An exemplary sliding pin 250 with a spherical head 252 is shown in detail in FIG. 17D. The spherical head 252 is adapted to be disposed within a complementary spherical recess 266 formed in a housing 265, as shown in FIG. 17C. The housing 265, which can include first and second portions 265a, 265b that fit together to close around the spherical head 252, can be sized to fit within and mate to a receiving head 262 of a bone screw 260 to allow polyaxial movement of the sliding pin 250 relative to the bone screw 260. While the configuration of the bone screw 260 can vary, in an exemplary embodiment, the bone screw 260 is a standard monoaxial bone screw. The housing halves 265a, 265b, when fit together, can have a substantially cylindrical shape that fits within the receiving head 262 of the bone screw 260. At least one of the housing halves, e.g., half 265b, can include a feature, such as a ridge or protrusion 267 formed therein and adapted to extend into one of the slots in the receiving head 262 to prevent rotational movement of the housing 265 with respect to the bone screw 260. Once disposed therein, a locking mechanism can be mated to the head 262 of the bone screw 260 to lock the housing 265 therein. In the illustrated exemplary embodiment shown in FIGS. 17A-17D, the locking mechanism is a set screw 268 that threads into the head 262 of the bone screw 260 to lock the housing 265 therein.

Figure 18A:
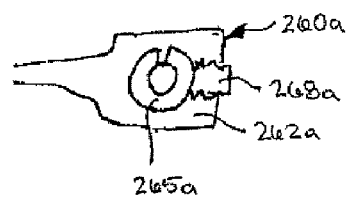
FIG. 18A is a partially cross-sectional side view of another embodiment of a bone screw for mating a sliding pin of a posterior stabilizing implant to a vertebra, showing a sleeve disposed within a head of the bone screw.
Figure 18B:
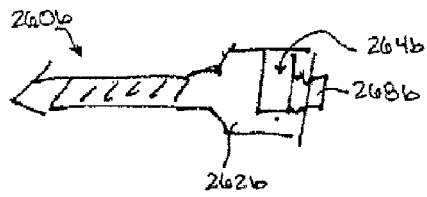
FIG. 18B is a partially cross-sectional side view of another embodiment of a bone screw for mating a sliding pin of a posterior stabilizing implant to a vertebra, showing a partial opening formed in a head of the bone screw for receiving a housing.
Figure 18C:
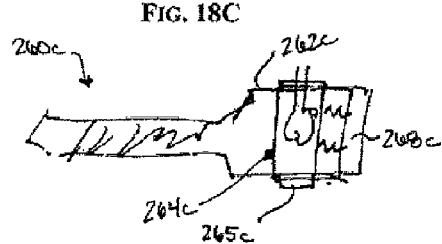
FIG. 18C is a partially cross-sectional side view of another embodiment of a bone screw for mating a sliding pin of a posterior stabilizing implant to a vertebra, showing an outer locking nut for engage a housing disposed within a head of the bone screw.
Figure 18D:
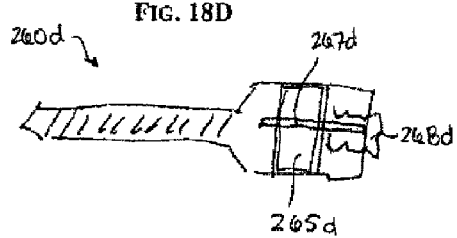
FIG. 18D is a partially cross-sectional side view of another embodiment of a bone screw for mating a sliding pin of a posterior stabilizing implant to a vertebra, showing an inner locking nut for engage a housing disposed within a head of the bone screw
Figure 18E:
FIG. 18E is a partially cross-sectional side view of another embodiment of a bone screw for mating a sliding pin of a posterior stabilizing implant to a vertebra, showing a clamp mechanism for engage a housing disposed within a head of the bone screw.
Figure 18F:
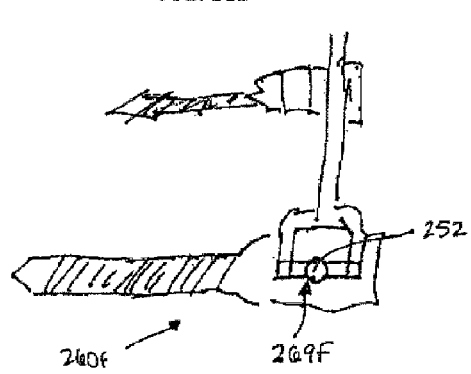
FIG. 18F is a partially cross-sectional side view of another embodiment of a bone screw for mating a sliding pin of a posterior stabilizing implant to a vertebra, showing a universal joint for allowing movement of a portion of a posterior stabilizing implant coupled thereto.

FIGS. 18A-18F illustrate additional exemplary techniques for dynamically mating the sliding pins of the second member to a vertebra. In the embodiment shown in FIG. 18A, the housing 265a is in the form of a sleeve that is removably disposed within the receiving head 262a of a bone screw 260a. The sleeve 265a has a longitudinal slit that allows the sleeve 265a to expand for receiving the spherical head 252 of the sliding pin 250. When the sleeve 265a and the spherical head 252 are disposed within the head 262a of the bone screw 260a, a locking mechanism, such as a set screw 268a, can be applied to the head 262a of the bone screw 260a lock the sleeve 265a therein. The sleeve 265a, like housing 265, can be configured to allow polyaxial movement of the sliding pin 250 relative thereto to provide a dynamic connection. In another embodiment, shown in FIG. 18B, the lateral opening 264b formed in the head 262b of the bone screw 260b can extend only partially therethrough, thus preventing the housing from passing completely through the head 262b of the bone screw 260b. FIG. 18C illustrates another embodiment in which the housing 265c has a length that is greater than a width of the head 262c of the bone screw 260c. As a result, the housing 265c extends from opposed ends of the lateral opening 264c in the bone screw 260c. Such a configuration allows an outer locking mechanism, e.g., an outer set screw 268c, to be applied to the head 262c of the bone screw 260c to engage the housing 265c. Alternatively, the locking mechanism 268d can include a pin member 267d or similar feature, as shown in FIG. 18D, for engaging the housing 265d to prevent movement of the housing 265d relative to the bone screw 260d. In another embodiment, as shown in FIG. 18E, the head 262e of the bone screw 260e can be in the form of a clamp mechanism that is adapted to engage the housing. FIG. 18F illustrates another embodiment in which a universal joint 269f is used to provide dynamic motion between the head 252 of the sliding pin and the bone screw 260f. A person skilled in the art will appreciate that a variety of other techniques can be used to provide a dynamic connection between the sliding pins and the bone screws.

In another exemplary embodiment, referring back to FIGS. 9A and 9B, the implant 200 can include one or more control members 270a, 270b for controlling movement between the first and second members 202a, 202b. The control members 270a, 270b can form a rigid stop to prevent extension of the adjacent vertebrae beyond a particular position, or they can form a compressive stop to limit or control extension of the adjacent vertebrae. In the illustrated exemplary embodiment, the first and second control members 270a, 270b are substantially cylindrical compressive members that are slidably disposed around the first and second sliding pins 210a, 210b, respectively. Each control member 270a, 270b can be disposed between the lateral member 202a, 202b and the bone screw 214a, 214b that mates the sliding pin 210a, 210b to the vertebrae. As a result, during extension or lateral bending of the vertebrae, the control members 270a, 270b are compressed as the sliding pins 210a, 210b slide into the lateral members 202a, 202b. The control members 270a, 270b can therefore limit or control extension and/or lateral bending. A person having ordinary skill in the art will appreciate that the properties, e.g., the size, shape, flexibility, etc., of the control members can be selected to obtain a desired result. Moreover, a kit containing several control members varying in property can be provided to allow a surgeon to select control members having the appropriate properties.

Figure 19A:
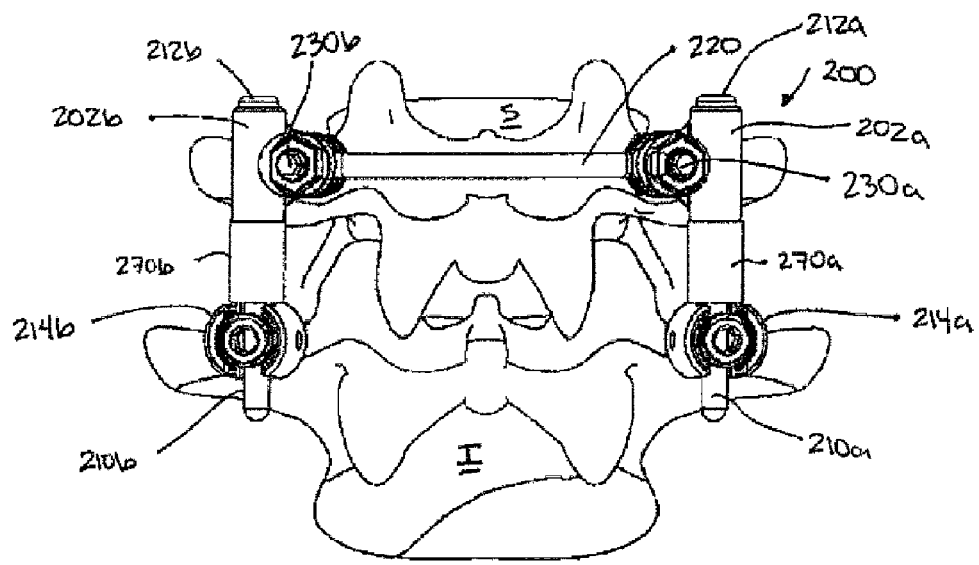
FIG. 19A is a posterior view of the posterior stabilizing implant shown in FIGS. 9A and 9B, showing the implant in use mated to adjacent vertebrae.
Figure 19B:
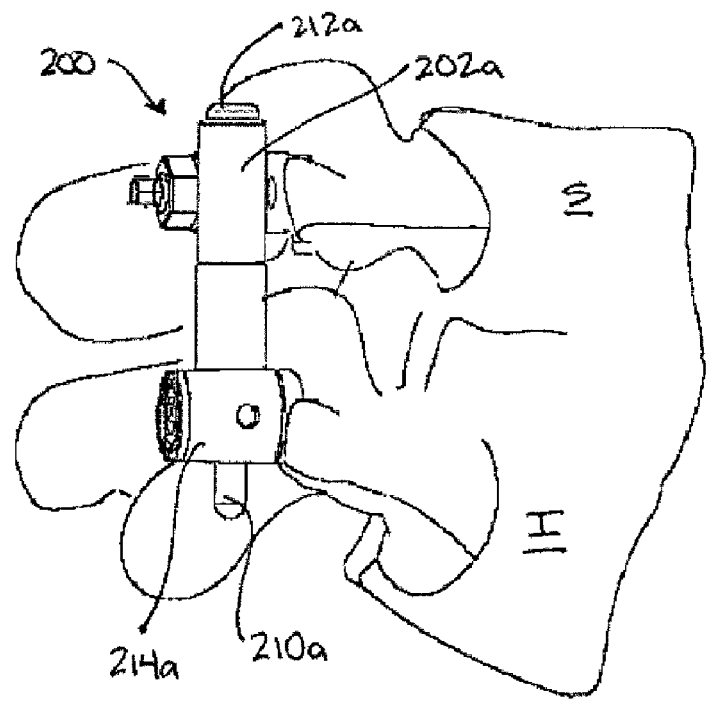
FIG. 19B is a side view of the implant and vertebrae shown in FIG. 19A.

FIGS. 19A and 19B illustrate the implant 200 coupled to adjacent superior (S) and inferior (/) vertebrae. The lateral members 202a, 202b of the first member 200a are coupled to one another by the connecting member 220, and the three components 202a, 202b, 220 are rigidly coupled to the superior vertebra S by two bone screws 230a, 230b implanted in the pedicles of the vertebra S. The sliding pins 210a, 210b are slidably disposed through the lateral members 202a, 202b and they are dynamically coupled to the inferior vertebra / by two polyaxial bone screws 214a, 214b implanted in the pedicles of the vertebra /. The configuration of the implant 200 is particularly advantageous in that it requires minimal, if any, resection of the facet joints due to the lateral positioning of the members 200a, 200b.

In use, the implant 200 allows lateral bending, flexion, and extension of the adjacent vertebrae S, /, preferably while limiting or substantially preventing axial rotation and shearing. In particular, flexion of the vertebrae S, / will cause the heads 212a, 212b of the sliding pins 210a, 210b to slide into the lateral members 202a, 202b until the heads 212a, 212b abut against the stop (e.g., shelf 205 shown in FIG. 10B). Although not shown, a spring or other compressive element could rest between shelf 205 and sliding pin 210a in order to provide some resistance to flexion. The amount of flexion can be adjusted by positioning the head 212a, 212b of each sliding pin 210a, 210b at a particular distance apart from the lateral members 202a, 202b. During extension and lateral bending of the adjacent vertebrae S, /, the lateral members 202a, 202b will move toward the second member 200b, thereby causing the control members 270a, 270b to be compressed between the lateral members 202a, 202b and the bone screws 214a, 214b. The property of each control member 270a, 270b can be designed to allow a certain amount of compression, for example, to mimic the natural function of the facet joints, thereby limiting extension and lateral bending of the adjacent vertebrae.

Figure 20A:
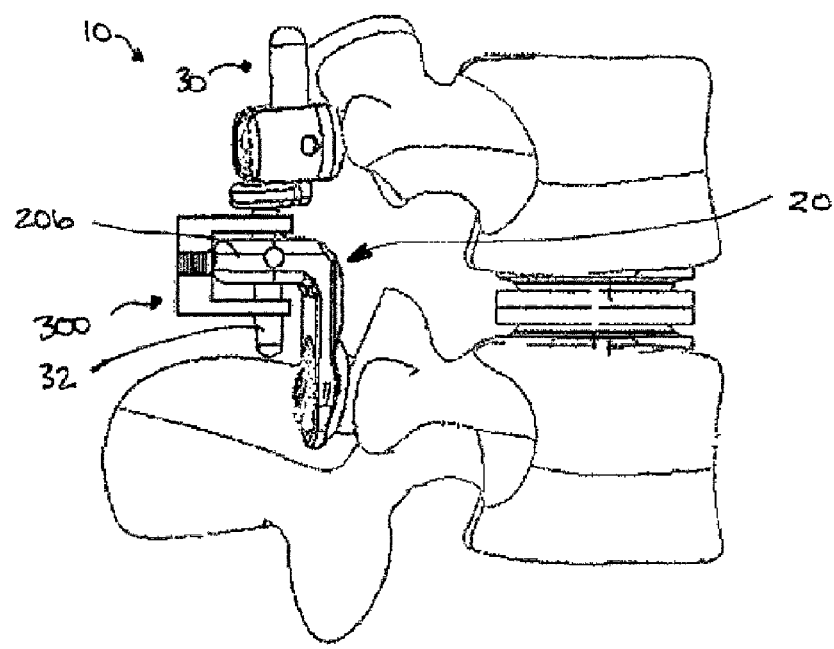
FIG. 20A is a side view of posterior stabilizing implant shown in FIG. 1B showing a locking mechanism adapted to prevent movement of the posterior stabilizing implant.
Figure 20B:
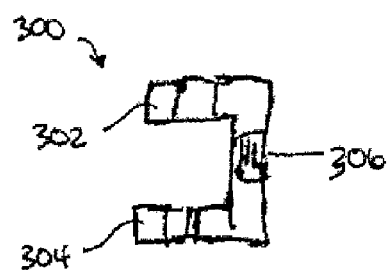
FIG. 20B is a side view of the locking mechanism shown in FIG. 20A.
Figure 20C:
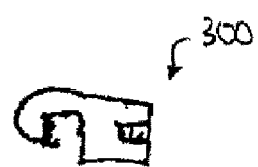
FIG. 20C is a top view of the locking mechanism shown in FIG. 20B.

In another embodiment, where movement of the adjacent vertebrae is not desired or is no longer necessary, a locking mechanism can be provided to prevent sliding movement of the first and second members of the posterior stabilizing implant relative to one another. By way of non-limiting example, FIGS. 20A-20C illustrate one exemplary embodiment of a technique for preventing movement between the moving components of a posterior stabilizing implant. The locking mechanism 300 is shown coupled to implant 10 of FIGS. 1A and 1B, however a person having ordinary skill in the art will appreciate that the locking mechanism can be adapted to use with any posterior stabilizing implant, or other implant in which it is desirable to prevent movement between two moving components. In the illustrated embodiment, the locking mechanism 300 includes first and second arms 302, 304 that are in the form of hooks that are adapted to be disposed around the extension rod 32 of the second member 30 on opposed sides of the second portion 20b of the first member 20. A set screw 306 or other locking element can be disposed through the locking mechanism 300 to engage or abut against the second portion 20b of the first member 20, thereby locking the hook-shaped arms 302, 304 relative to the extension rod 32. As a result, slidable movement of the extension rod 32 with respect to the first member 20 is substantially prevented or limited. A person skilled in the art will appreciate that the distance between the first and second arms 302, 304 can to allow some limited movement to occur.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An implant for stabilizing the spine, comprising:
   a first member having first and second lateral portions and a connecting member extending between and coupled to the first and second lateral portions, the first member being adapted to rigidly couple to a first vertebra;
   a second member having a first component adapted to rigidly mate to a second vertebra adjacent to the first vertebra, and a second component slidably disposed through and movably coupled to the first component and the first member, and;
   at least one compressive member disposed between the first and second members and adapted to compress to limit extension of first and second vertebrae coupled to the first and second members;
   wherein the first and second members are adapted to allow flexion, extension, and lateral bending and to substantially restrict posterior-anterior shear and rotation of first and second vertebrae when the first member is rigidly coupled to the first vertebra and the first component of the second member is rigidly coupled to the second vertebra.

2. The implant of claim 1, wherein the second component comprises a first pin member slidably disposed through the first lateral portion, and a second pin member slidably disposed through the second lateral portion.

3. The implant of claim 2, wherein the first pin member includes a head formed on a first terminal end thereof and adapted to be received within a portion of a lumen in the first lateral portion, and wherein the second pin member includes a head formed on a first terminal end thereof and adapted to be received within a portion of a lumen in the second lateral portion.

4. The implant of claim 3, wherein the lumens in the first and second lateral portions each include stop formed therein and adapted to limit slidable movement of the head of the pin member.

5. The implant of claim 3, wherein the first component comprises a fastening element having a rod-receiving head thereon, and wherein a second terminal end of each of the first and second pin members is slidably disposed through the rod-receiving head of the fastening element.

6. The implant of claim 1, wherein the connecting member comprises an elongate bar having opposed terminal ends that are adapted to mate to the first and second lateral portions.

7. The implant of claim 6, wherein the first and second lateral portions include offset connectors formed thereon, and wherein the offset connectors and the opposed terminal ends of the connecting member include bores formed therein for receiving a bone screw to mate the first member to a first vertebra.

8. The implant of claim 7, further comprising at least one angled washer adapted to position a bone screw at an angle relative to an axis of the bore in at least one of the terminal ends of the connecting member.

9. The implant of claim 7, further comprising at least one polyaxial washer adapted to position a bone screw at an angle relative to an axis of the bore in at least one of the terminal ends of the connecting member.

10. The implant of claim 1, wherein the first component of the second member comprises a bone anchor having a bone engaging portion and a U-shaped receiving head that seats the second component of the second member.

11. An implant for stabilizing the spine, comprising:
a first member having a first portion adapted to rigidly couple to a first vertebra, and a second portion slidably movable through the first portion and adapted to couple to a second vertebra, the first member including a stop member formed therein for limiting slidable movement of the second portion relative to the first portion;
a second member having a first portion adapted to rigidly couple to a first vertebra, and a second portion slidably movable through the first portion and adapted to couple to a second vertebra; and
a connecting member extending between and coupled to the first and second members, opposed terminal ends of the connecting member having a bore formed therein for receiving a bone screw to rigidly couple the connecting member and the first and second portions of the first and second members to the first vertebra;
wherein the first and second members are configured to controllably allow flexion, extension, and lateral bending and to substantially restrict posterior-anterior shear and rotation of first and second vertebrae coupled thereto.

12. The implant of claim 11, wherein the second portion of each of the first and second members comprises a pin member that is slidably disposed through the first portion.

13. The implant of claim 12, wherein the first and second members each further comprise a bone screw having a polyaxial head that slidably receives the pin member to mate the pin member to a second vertebra.

14. The implant of claim 12, wherein each pin member includes a spherical member formed on a terminal end thereof, and wherein the first and second members each further comprise a bone screw having a head that is adapted to polyaxially receive the spherical member of the pin member to mate the pin member to a second vertebra.

15. The implant of claim 12, wherein each pin member includes a head that is adapted to be received within a lumen formed in the first portion of each of the first and second members, and wherein each lumen includes an enlarged diameter region adapted to receive the head of the pin member.

16. The implant of claim 11, wherein the first portion of each of the first and second members includes an offset connector formed thereon and adapted to mate to the connecting member.

17. The implant of claim 11, wherein the first and second members each further comprise a compressible member disposed around a portion of the second portion and adapted to compress upon slidable movement of the second portion relative to the first portion.

18. The implant of claim 11, wherein the connecting member is coupled to and extends between the first portion of the first member and the first portion of the second member.

* * * * *